(12) United States Patent
Athanasiadis et al.

(10) Patent No.: US 8,809,301 B2
(45) Date of Patent: Aug. 19, 2014

(54) SURGICAL HYDROGEL

(71) Applicant: Medtronic Xomed, Inc., Jacksonville, FL (US)

(72) Inventors: Theodore Athanasiadis, Goodwood (AU); Lyall Robert Hanton, Dunedin (NZ); Stephen Carl Moratti, Dunedin (NZ); Brian Harford Robinson, Dunedin (NZ); Simon Rae Robinson, Wellington (NZ); Zheng Shi, Dunedin (NZ); James Simpson, Dunedin (NZ); Peter John Wormald, North Adelaide (AU)

(73) Assignees: Adelaide Research & Innovation Pty Ltd, Adelaide (AU); Robinson Squidgel Ltd, Dunedin (NZ); Otago Innovation Ltd, Dunedin (NZ)

( * ) Notice: Subject to any disclaimer, the term of this patent is extended or adjusted under 35 U.S.C. 154(b) by 0 days.

(21) Appl. No.: 13/886,659

(22) Filed: May 3, 2013

(65) Prior Publication Data
US 2013/0244974 A1 Sep. 19, 2013

Related U.S. Application Data

(63) Continuation of application No. 12/675,329, filed as application No. PCT/NZ2008/000219 on Aug. 26, 2008, now abandoned.

(60) Provisional application No. 60/968,414, filed on Aug. 28, 2007.

(51) Int. Cl.
*A01N 43/04* (2006.01)

(52) U.S. Cl.
USPC .............................................. 514/55; 536/20

(58) Field of Classification Search
CPC ..... C08L 5/08; A61L 26/0052; A61L 31/041; A61L 2400/04; A61L 26/008; A61L 31/145; C08B 37/0063
USPC .............................................. 514/55; 536/20
See application file for complete search history.

(56) References Cited

U.S. PATENT DOCUMENTS

| | | | |
|---|---|---|---|
| 4,895,724 A | 1/1990 | Cardinal et al. | |
| 5,599,916 A | 2/1997 | Dutkiewicz et al. | |
| 5,679,658 A | 10/1997 | Elson | |
| 5,747,475 A | 5/1998 | Nordquist et al. | |
| 5,770,229 A | 6/1998 | Tanikara et al. | |
| 5,788,959 A | 8/1998 | Singh | |
| 5,836,970 A | 11/1998 | Pandit | |
| 5,840,341 A | 11/1998 | Watts et al. | |
| 5,888,988 A | 3/1999 | Elson | |
| 5,902,798 A | 5/1999 | Gonda et al. | |
| 6,444,797 B1 | 9/2002 | Son et al. | |
| 6,486,140 B2 | 11/2002 | Hansson et al. | |
| 6,514,522 B2 | 2/2003 | Domb | |
| 6,566,406 B1 | 5/2003 | Pathak et al. | |
| 7,098,194 B2 | 8/2006 | Chenite et al. | |
| 7,834,065 B2 | 11/2010 | Nakajima et al. | |
| 2002/0193812 A1* | 12/2002 | Patel et al. ................. | 606/151 |
| 2005/0002893 A1 | 1/2005 | Goldmann | |
| 2006/0134185 A1* | 6/2006 | Odermatt et al. ............ | 424/443 |
| 2006/0292030 A1 | 12/2006 | Odermatt et al. | |
| 2007/0202142 A1 | 8/2007 | Laugier et al. | |
| 2007/0243130 A1 | 10/2007 | Chen et al. | |
| 2007/0243131 A1 | 10/2007 | Chen et al. | |
| 2008/0075657 A1 | 3/2008 | Abrahams et al. | |
| 2008/0319101 A1 | 12/2008 | Nakajima et al. | |

FOREIGN PATENT DOCUMENTS

| | | |
|---|---|---|
| EP | 1 849 486 | 10/2007 |
| JP | 03-165775 | 7/1991 |
| WO | WO 96/02258 A1 | 2/1996 |
| WO | WO 96/02260 | 2/1996 |
| WO | WO 96/35433 | 11/1996 |
| WO | WO 98/22114 | 5/1998 |
| WO | WO 2004/006961 A1 | 1/2004 |
| WO | WO 2004/026200 A2 | 4/2004 |
| WO | WO 2006/080523 A1 | 8/2006 |
| WO | WO 2008/067655 A1 | 6/2008 |
| WO | WO 2009/132228 A1 | 10/2009 |

OTHER PUBLICATIONS

Kato et al ("N-succinyl-chitosan as a drug carrier:water-insoluble and water-soluble conjugates," Biomaterials 25 (2004) 907-915).*
Kuroyanagi, Y. et al., "Development of a new wound dressing with antimicrobial delivery capability", The Wound Healing Society, Wound Repair and Regeneration, vol. 2, No. 2, pp. 122-129 (1994).
Kato et al., "N-succinyl-chitosan as a drug carrier: water-insoluble and water-soluble conjugates," Biomaterials 25, 907-915 (2004).
Fini, A. et al., "The Role of Chitosan in Drug Delivery", Healthcare Technology Review, Am. J. Drug Deliv. 1(1): 43-59 (2003).
Kato et al., "Contribution of Chitosan and its Derivatives to Cancer Chemotherapy", in vivo 19: 301-310 (2005).
M.N.V. Ravi Kumar, "A review of chitin and chitosan applications", Reactive & Functional Polymers 46, pp. 1-27 (2000).
Sato, M. et al., "In Vivo, Drug Release and Antitumor Characteristics of Water-Soluble Conjugates of Mitomycin C. with Glycol-Chitosan and N-Succinyl-Chitosan", Biol. Pharm. Bull. vol. 19, No. 9, pp. 1170-1177 (1996).
Yan, C. et al., "Nanoparticles of 5-fluorouracil (5-FU) loaded and N-succinyl-chitosan (Suc-Chi) for cancer chemotherapy: preparation, characterization—in-vitro drug release and anti-tumour activity", Journal of Pharmacy and Pharmacology, vol. 58, No. 9, pp. 1177-1181 (2006).

(Continued)

*Primary Examiner* — Suzanne Ziska
(74) *Attorney, Agent, or Firm* — Seed IP Law Group PLLC

(57) ABSTRACT

A composition suitable for use in wound healing, particularly for reducing post-surgical adhesions, containing cross-linked derivatives of chitosan and dextran polymers. A hydrogel forms when solutions of the polymers are combined.

19 Claims, 14 Drawing Sheets

(56) References Cited

OTHER PUBLICATIONS

Weng, L. et al., "Rheological Characterization of in Situ Crosslinkable Hydrogels Formulated from Oxidized Dextran and N-Carboxyethyl Chitosan", Biomacromolecules, vol. 8, pp. 1109-1115 (2007).

Zhang, Zhi-Liang et al., "Preventive effects of chitosan on peritoneal adhesion in rats", World Journal of Gastroenterology, vol. 12, No. 28, pp. 4572-4577 (Jul. 28, 2006).

Zhou, Juan et al., "Reduction in postoperative adhesion formation and re-formation after an abdominal operation with the use of N, O-carboxymethyl chitosan", Surgery, vol. 135, No. 3, pp. 307-312 (Mar. 2004).

"Spray Gel Adhesion Barrier" Information Sheet, Confluent Surgical, Inc., 1 page (2004).

Kennedy, Renee et al., "Prevention of experimental postoperative peritoneal adhesions by N,O-carboxymethyl chitosan", Surgery, vol. 120, No. 5, pp. 866-870 (Nov. 1996).

Krause, Tyrone J. et al., "Prevention of Pericardial Adhesions with N—O Carboxymethychitosan in the Rabbit Model", informa healthcare, Summary Journal of Investigative Surgery, 1 page (2001).

Ito, Taichi et al., Dextran-based in situ cross-linked injectable hydrogels to prevent peritoneal adhesions, Biomaterials, vol. 28, pp. 3418-3426 (2007).

Diamond, Michael P. et al., "Reduction of postoperative adhesions by N, O-carboxymethylchitosan: a pilot study", Fertility and Sterility®, vol. 80, No. 3, pp. 631-636 (2003).

Costain, Darren J. et al., "Prevention of postsurgical adhesions with N, O-carboxymethyl chitosan: Examination of the efficacious preparation and the effect of N, O-carboxymethyl chitosan on postsurgical healing", Surgery, vol. 121, No. 3, pp. 314-319 (Mar. 1997).

M. Ruiz Planas, Thesis entitled "Development of techniques based on natural polymers for the recovery of precious metals", title page and Chapter 3, "The Sorbents: Chitin, Chitosan and Derivatives", pp. 53-76 (Apr. 2002), downloaded from the Internet at: www.tdx.cat/bitstream/handle/10803/6426/01TITOL.pdf?sequence=1 and www.tdx.cat/bitstream/handle/10803/6426/05CAPITOL3.pdf?sequence=5.

Tan, Huaping et al., "Injectable in situ forming biodegradable chitosan-hyaluronic acid based hydrogels for cartilage tissue engineering", Biomaterials, vol. 30, pp. 2499-2506 (2009).

\* cited by examiner

SURGICAL HYDROGEL

CROSS REFERENCE TO RELATED APPLICATIONS

This application is a Continuation of U.S. application Ser. No. 12/675,329 filed 4 Aug. 2010, which is in turn an application under 35 U.S.C. §371 of International Application No. PCT/NZ2008/000219 filed 26 Aug. 2008, which in turn claims priority to U.S. Provisional Application Ser. No. 60/968,414 filed 28 Aug. 2007, the disclosures of each of which are incorporated herein by reference.

BACKGROUND OF THE INVENTION

The formation of adhesions is a frequent and unfortunate result of many surgeries. Adhesions are fibrous bands connecting tissue surfaces that are normally separated. Adhesions are particularly common following abdominal and pelvic surgeries such as hernia repair, gynaecological surgeries and colorectal surgeries.

Trauma to the tissue caused by handling and drying during surgery causes a fibrinous exudate to be released. If the exudate is not absorbed or lysed, it may collect in the peritoneal or pelvic cavity where it is converted into an adhesion. The exudate becomes ingrown with fibroblasts, collagen is deposited and blood vessels begin to form, allowing organisation of the adhesion.

The formation of adhesions can lead to serious complications such as small bowel obstruction, female infertility and chronic pain. Patients may need to undergo further surgery to dissect adhesions, with no guarantees that new adhesions will not form.

Techniques to reduce adhesion formation include lavage of the peritoneal cavity, administration of pharmacological agents and mechanical separation of the tissues. Post-operative hemostasis, the physiologic process whereby bleeding is halted, can also decrease the risk of adhesion formation, as well as conferring other benefits.

Unfortunately, current procedures for reducing adhesions and/or achieving hemostasis are not particularly effective and can be unpleasant for the patient. In addition, in some circumstances treatments aimed at hemostasis may increase the risk of adhesion formation.

For example, following endoscopic sinus surgery (ESS) used to treat chronic sinusitis, patients must endure uncomfortable nasal packing to control bleeding. However, removal of the nasal packs can cause mucosal trauma which increases the likelihood that adhesions will form. Studies have shown that even dressings incorporating known topical hemostatic agents such as thrombin, fibrin, fibrinogen and collagen can cause a significant increase in the formation of adhesions (see for example, Chandra R. K., Kern R. C., Advantages and disadvantages of topical packing in endoscopic sinus surgery, *Curr Opin Otolaryngol Head Neck Surg* 2004, 12, 21-26). Adhesion formation requiring further surgery occurs in 10-30% of patients undergoing ESS.

Polymer solutions and gels have been applied to target areas to reduce adhesions. For example, gels have been used to coat surgically exposed tissues before closing the surgical site. Some approaches allow for the polymers to be added to the patient in situ, in a solution and then chemically reacted to form covalent cross-links so as to create a polymer network. For example, SprayGel™ is a PEG-based material that forms an adhesion barrier when applied to tissue.

Polysaccharide polymers such as chitosan are also well known as gel forming medicinal agents. Chitosan is recognised to have wound healing properties. For example, U.S. Pat. No. 5,836,970 discloses chitosan and alginate wound dressings that may be prepared as fibers, powders, films, foams, or water-swellable hydrocolloids. U.S. Pat. No. 5,599,916 discloses a water-swellable, water-insoluble chitosan salt that can be used in wound dressings, and U.S. Pat. No. 6,444,797 discloses a chitosan microflake that can be used as a wound dressing or skin coating.

Chitosan has also been shown to have a preventative effect on peritoneal adhesion in rats (Preventive effects of chitosan on peritoneal adhesion in rats, Zhang, Zhi-Liang et al., World J Gastroenterol, 2006, 12(28) 4572-4577.

Derivatives of chitosan have also been investigated for their effects on wound-healing and adhesion prevention. For example, PCT publication WO 96/35433 describes the use of N,O-carboxymethylchitosan for the prevention of surgical adhesions. N,O-carboxymethylchitosan has also been discussed in:

(i) Kennedy, R. et al., Prevention of experimental postoperative adhesions by N,O-carboxymethyl chitosan, Surgery, 1996, 120, 866-70;
(ii) Costain, D. J. et al., Prevention of postsurgical adhesions with N,O-carboxymethylchitosan: Examination of the most efficacious preparation and the effect of N,O-carboxymethyl chitosan on postsurgical healing, Surgery, 1997; 121, 314-9;
(iii) Krause, T. J. et al., Prevention of pericardial adhesions with N,O-arboxymethylchitosan in the Rat Model, Journal of Investigative Surgery, 2001, 14, 93-97;
(iv) Diamond, Michael P. et al., Reduction of postoperative adhesions by N,O-arboxymethylchitosan: a pilot study, Fertil Steril 2003, 80, 631-636;
(v) Diamond, Michael P. et al., Reduction of post operative adhesions by N,O-carboxymethylchitosan: A Pilot Study, The Journal of the American Association of Gynecologic Laparoscopists, 2004, 11(1), 127; and
(vi) Lee, Timothy D. G. et al., Reduction in postoperative adhesion formation and re-formation after an abdominal operation with the use of N,O-carboxymethyl chitosan, Surgery, 2004, 135, 307-312.

PCT publication WO 98/22114 discusses the use of chitosan combined with sulphated mono-, di-, or oligo-saccharides for enhancing wound healing in collagen-containing tissues. PCT publication WO 96/02260 describes chitosan in combination with heparin, heparin sulphate or dextran sulphate. This combination is said to promote healing of dermal wounds.

PCT publication WO 04/006961 describes a gel for immobilizing and encapsulating cells formed by cross-linking neutral chitosan with a bifunctional multifunctional aldehyde or aldehyde-treated hydroxyl-containing polymer.

Despite these efforts, adhesion formation still commonly occurs in many areas of surgery. Therefore, there is still a need a great need for new polymeric materials with medical efficacy for hemostasis and adhesion prevention that can be used to improve surgical outcomes.

Accordingly, it is an object of the invention to provide a hydrogel that can be applied to a wound to assist wound healing, or to provide the public with a useful choice.

SUMMARY OF THE INVENTION

The invention relates to a hydrogel that can be applied to surgical and other wounds. The hydrogel can be made by combining aqueous solutions of two polymers which cross-link to form a polymer network when mixed. As cross-linking occurs, the resulting polymer network forms a hydrogel in aqueous solution. The hydrogel can be formed in situ, for example, by spraying, squirting or pouring the polymer solutions onto the target area. Alternatively, the hydrogel can be pre-formed, then applied to the target area. In another embodiment, the hydrogel can be formed when a wound dressing incorporating the polymer components is moistened.

Hydrogels of the invention assist in wound healing and may help prevent adhesions forming between neighbouring tissues that have been damaged so as to make them susceptible to adhesion formation. Hydrogels of the invention may also affect haemostasis by reducing or stopping bleeding of a wound. The hydrogels are biodegradable under surgical conditions and will break down gradually over a period of days or weeks.

In one aspect the invention provides a polymer network comprising a dicarboxy-derivatized chitosan polymer cross-linked to an aldehyde-derivatized dextran polymer.

In another aspect the invention provides a polymer network consisting of a dicarboxy-derivatized chitosan polymer cross-linked to an aldehyde-derivatized dextran polymer.

In one embodiment of the above aspects the dicarboxy-derivatized chitosan polymer is cross-linked to the aldehyde-derivatized dextran polymer through the amine group of the dicarboxy-derivatized chitosan polymer and the aldehyde group of the aldehyde-derivatized dextran polymer.

In one embodiment of the above aspects the dicarboxy-derivatized chitosan polymer is an N-succinyl chitosan polymer.

In another aspect the invention provides a polymer network comprising N-succinyl chitosan cross-linked to an aldehyde-derivatized dextran polymer.

In another aspect the invention provides a polymer network consisting of N-succinyl chitosan cross-linked to an aldehyde-derivatized dextran polymer.

In one embodiment of the above aspects the N-succinyl chitosan is cross-linked to the aldehyde-derivatized dextran polymer through the amine group of the N-succinyl chitosan and the aldehyde group of the aldehyde-derivatized dextran polymer.

In another aspect the invention provides a polymer network comprising a dicarboxy-derivatized chitosan polymer cross-linked to an aldehyde-derivatized dextran polymer, wherein the polymer network forms a hydrogel within about 1 sec to about 5 minutes of mixing the dicarboxy-derivatized chitosan polymer and the aldehyde-derivatized dextran polymer in aqueous solution.

In another aspect the invention provides a polymer network comprising N-succinyl chitosan cross-linked to an aldehyde-derivatized dextran polymer, wherein the polymer network forms a hydrogel within about 1 sec to about 5 minutes of mixing the N-succinyl chitosan and the aldehyde-derivatized dextran polymer in aqueous solution.

In one embodiment the hydrogel forms within about 1 sec to about 30 sec, preferably within about 1 sec to about 20 sec, more preferably within about 1 sec to about 10 sec. In another embodiment the hydrogel forms within about 30 sec to about 5 minutes. In another embodiment, the hydrogel forms within about 5 sec to about 1 min.

In another aspect the invention provides a polymer network comprising a dicarboxy-derivatized chitosan polymer cross-linked to an aldehyde-derivatized dextran polymer, wherein the polymer network forms a hydrogel within about 5 minutes to about 20 minutes of mixing the dicarboxy-derivatized chitosan polymer and the aldehyde-derivatized dextran polymer in aqueous solution.

In another aspect the invention provides a polymer network comprising N-succinyl chitosan cross-linked to an aldehyde-derivatized dextran polymer, wherein the polymer network forms a hydrogel within about 5 minutes to about 20 minutes of mixing the N-succinyl chitosan and the aldehyde-derivatized dextran polymer in aqueous solution.

In one embodiment the hydrogel forms within about 5 minutes to about 10 minutes.

In another embodiment the hydrogel forms within about 10 minutes to about 20 minutes.

In another aspect the invention provides a polymer network comprising a dicarboxy-derivatized chitosan polymer cross-linked to an aldehyde-derivatized dextran polymer, wherein the polymer network forms a hydrogel within about 20 minutes to about 2 hours of mixing the dicarboxy-derivatized chitosan polymer and the aldehyde-derivatized dextran polymer in aqueous solution.

In another aspect the invention provides a polymer network comprising N-succinyl chitosan cross-linked to an aldehyde-derivatized dextran polymer, wherein the polymer network forms a hydrogel within about 20 minutes to about 2 hours of mixing the N-succinyl chitosan and the aldehyde-derivatized dextran polymer in aqueous solution.

In one embodiment the hydrogel forms within about 20 minutes to about 2 hours, preferably within about 30 minutes to about 1 hour.

In one aspect the invention provides a wound healing composition comprising a dicarboxy-derivatized chitosan polymer and an aldehyde-derivatized dextran polymer in aqueous solution.

In one embodiment the dicarboxy-derivative is N-succinyl chitosan.

In one embodiment the composition comprises between about 2% to 10% w/v dicarboxy-derivatized chitosan polymer. In one embodiment, the composition comprises between about 2% to 10% w/v aldehyde-derivatized dextran polymer.

In another aspect the invention provides a hydrogel comprising a dicarboxy-derivatized chitosan polymer cross-linked to an aldehyde-derivatized dextran polymer in aqueous solution.

In one embodiment the hydrogel comprises between about 2% to about 10% w/v dicarboxy-derivatized chitosan polymer. In one embodiment the hydrogel comprises between about 2% to about 10% w/v aldehyde-derivatized dextran polymer.

Preferably, the hydrogel comprises between about 2% to about 8% w/v, more preferably between about 2% to about 6% w/v dicarboxy-derivatized chitosan polymer. Most preferably, the hydrogel comprises about 5% w/v dicarboxy-derivatized chitosan polymer.

Preferably, the hydrogel comprises between about 2% to about 8% w/v, more preferably between about 2% to about 6% w/v aldehyde-derivatized dextran polymer. Most preferably, the hydrogel comprises about 5% w/v aldehyde-derivatized dextran polymer.

In one embodiment the dicarboxy-derivatized chitosan polymer is N-succinyl chitosan.

In one embodiment, the aqueous solution is selected from the group comprising water, saline, buffer and mixtures thereof. Preferably, the aqueous solution is about 0.9% w/v saline solution.

In another aspect the invention provides a method of producing a polymer network comprising a dicarboxy-derivatized chitosan polymer cross-linked to an aldehyde-derivatized dextran polymer, wherein the method comprises mixing an aqueous solution of a dicarboxy-derivatized chitosan polymer with an aqueous solution of an aldehyde-derivatized dextran polymer.

In one embodiment the aqueous solution of dicarboxy-derivatized chitosan polymer comprises between about 2% to about 10% w/v of a dicarboxy-derivatized chitosan polymer. Preferably, the aqueous solution comprises between about 2% to about 8% w/v, more preferably about 5% w/v of a dicarboxy-derivatized chitosan polymer.

In one embodiment the aqueous solution of dicarboxy-derivatized chitosan polymer has a pH of between about 6 to 8. Preferably, the aqueous solution of dicarboxy-derivatized chitosan polymer has a pH between about 6.5 to 7.5.

In one embodiment the dicarboxy-derivatized chitosan is N-succinyl chitosan.

In one embodiment the aqueous solution of aldehyde-derivatized dextran polymer comprises between about 2% to about 10% w/v of an aldehyde-derivatized dextran polymer. Preferably, the aqueous solution comprises between about 2% to about 8% w/v, more preferably, about 5% w/v of an aldehyde-derivatized dextran polymer.

In one embodiment the aqueous solution of aldehyde-derivatized dextran polymer has a pH of between about 6 to 8. Preferably, the aqueous solution of aldehyde-derivatized dextran polymer has a pH of between about 6.5 to 7.5.

In one embodiment the aldehyde-derivatized dextran polymer is 50-100% aldehyde-derivatized, preferably 70-100% aldehyde-derivatized, more preferably 80-100% aldehyde-derivatized.

In one embodiment the method comprises mixing equal volumes of aqueous solutions of (a) a dicarboxy-derivatized chitosan polymer, and (b) an aldehyde-derivatized dextran polymer.

In one embodiment the polymer network and aqueous solution together comprise a hydrogel.

In one embodiment the aqueous solutions of polymers are mixed by stirring the solutions together. In another embodiment, the aqueous solutions of polymers are mixed as they are applied to a target area, such as by simultaneously spraying, squirting or pouring the solutions onto the target area.

In one embodiment, the aqueous solution is selected from the group comprising water, saline, buffer and mixtures thereof. Preferably, the aqueous solution is about 0.9% w/v saline solution.

In one embodiment, the aqueous solutions of polymers may contain one or more pharmaceutically acceptable excipients.

In one aspect the invention provides a hydrogel comprising a dicarboxy-derivatized chitosan polymer cross-linked to an aldehyde-derivatized dextran polymer wherein the hydrogel comprises one or more biologically active agents.

In one embodiment the one or more biologically active agents are selected from the group comprising plasma proteins, hormones, enzymes, antibiotics, antiseptic agents, antineoplastic agents, antifungal agents, antiviral agents, anti-inflammatory agents, local anaesthetics, growth factors, steroids, cell suspensions, cytotoxins, and cell proliferation inhibitors.

In one aspect the invention provides a hydrogel comprising a dicarboxy-derivatized chitosan polymer cross-linked to an aldehyde-derivatized dextran polymer wherein the hydrogel comprises one or more non-biologically active agents.

In one embodiment the one or more non-biologically active agents are selected from the group comprising thickeners and dyes.

In one aspect the invention provides a method of preventing or reducing adhesion of tissue susceptible to adhesion formation, comprising treating the tissue with a hydrogel of the invention.

In one embodiment the adhesion is post-surgical adhesion.

In one embodiment the method comprises applying to the tissue a hydrogel of the invention. Preferably, a layer of the hydrogel is spread over the surface of the tissue.

In one embodiment the method comprises applying to the tissue (a) an aqueous solution of a dicarboxy-derivatized chitosan polymer and (b) an aqueous solution of an aldehyde-derivatized dextran polymer such that (a) and (b) combine to form the hydrogel on the surface of the tissue.

In one embodiment (a) and (b) are simultaneously applied to the tissue.

In one embodiment (a) and (b) are simultaneously sprayed onto the tissue. In one embodiment (a) and (b) are simultaneously squirted onto the tissue. In another embodiment (a) and (b) are simultaneously poured onto the tissue.

In another aspect the invention provides a method of preventing or reducing post-surgical adhesion of tissue susceptible to adhesion formation comprising treating the tissue with a hydrogel of the invention, wherein the method comprises applying to the tissue (a) an aqueous solution of an dicarboxy-derivatized chitosan polymer and (b) an aqueous solution of an aldehyde-derivatized dextran polymer such that (a) and (b) combine to form the hydrogel on the surface of the tissue.

In another aspect the invention provides a method of accelerating or promoting wound healing comprising treating the wound with a hydrogel of the invention.

In one embodiment the method comprises applying to the wound a hydrogel of the invention. Preferably, a layer of the hydrogel is spread over the surface of the wound.

In one embodiment the method comprises applying to the wound (a) an aqueous solution of an dicarboxy-derivatized chitosan polymer and (b) an aqueous solution of an aldehyde-derivatized dextran polymer such that (a) and (b) combine to form the hydrogel.

In one embodiment (a) and (b) are simultaneously applied to the wound.

In one embodiment (a) and (b) are simultaneously sprayed onto the wound. In one embodiment (a) and (b) are simultaneously squirted onto the wound. In another embodiment (a) and (b) are simultaneously poured onto the wound.

In another aspect the invention provides a method of accelerating or promoting wound healing comprising treating the wound with a hydrogel of the invention, wherein the method comprises applying to the wound (a) an aqueous solution of an dicarboxy-derivatized chitosan polymer and (b) an aqueous solution of an aldehyde-derivatized dextran polymer such that (a) and (b) combine to form the hydrogel on the surface of the wound.

In another aspect the invention provides a method of reducing or stopping bleeding of a wound comprising treating the wound with a hydrogel of the invention.

In one embodiment the method comprises applying to the wound a hydrogel of the invention. Preferably, a layer of the hydrogel is spread over the surface of the wound.

In one embodiment the method comprises applying to the wound (a) an aqueous solution of an dicarboxy-derivatized chitosan polymer and (b) an aqueous solution of an aldehyde-derivatized dextran polymer such that (a) and (b) combine to form the hydrogel.

In one embodiment (a) and (b) are simultaneously applied to the wound.

In one embodiment (a) and (b) are simultaneously sprayed onto the wound. In one embodiment (a) and (b) are simultaneously squirted onto the wound. In another embodiment (a) and (b) are simultaneously poured onto the wound.

In another aspect the invention provides a method of reducing or stopping bleeding of a wound comprising treating the wound with a hydrogel of the invention, wherein the method comprises applying to the wound (a) an aqueous solution of an dicarboxy-derivatized chitosan polymer and (b) an aqueous solution of an aldehyde-derivatized dextran polymer such that (a) and (b) combine to form the hydrogel on the surface of the wound.

In another aspect the invention provides a method of delivering one or more biologically active agents to a tissue comprising treating the tissue with a hydrogel of the invention, wherein the hydrogel comprises one or more biologically active agents.

In one embodiment the method comprises applying to the tissue a hydrogel of the invention, wherein the hydrogel comprises one or more biologically active agents. Preferably, a layer of the hydrogel is spread over the surface of the tissue.

In one embodiment the method comprises applying to the tissue (a) an aqueous solution of a dicarboxy-derivatized chitosan polymer and (b) an aqueous solution of an aldehyde-derivatized dextran polymer such that (a) and (b) combine to form the hydrogel on the surface of the tissue, wherein one or both of (a) and (b) include one or more biologically active agents.

In one aspect the invention provides a use of a hydrogel of the invention in the manufacture of a medicament for preventing or reducing post-surgical adhesion of tissue susceptible to adhesion formation.

In another aspect the invention provides a use of (a) an aqueous solution of a dicarboxy-derivatized chitosan polymer and (b) an aqueous solution of an aldehyde-derivatized dextran polymer in the manufacture of a medicament for preventing or reducing adhesion of tissue susceptible to adhesion formation, wherein (a) and (b) combine to form a hydrogel of the invention.

In another aspect the invention provides a use of a hydrogel of the invention in the manufacture of a medicament for accelerating or promoting wound healing.

In another aspect the invention provides a use of (a) an aqueous solution of a dicarboxy-derivatized chitosan polymer and (b) an aqueous solution of an aldehyde-derivatized dextran polymer in the manufacture of a medicament for accelerating or promoting wound healing, wherein (a) and (b) combine to form a hydrogel of the invention.

In another aspect the invention provides a use of a hydrogel of the invention in the manufacture of a medicament for reducing or stopping bleeding of a wound.

In another aspect the invention provides a use of (a) an aqueous solution of a dicarboxy-derivatized chitosan polymer and (b) an aqueous solution of an aldehyde-derivatized dextran polymer in the manufacture of a medicament for reducing or stopping bleeding of a wound, wherein (a) and (b) combine to form a hydrogel of the invention.

In another aspect the invention provides a use of a hydrogel of the invention in the manufacture of a medicament for delivering one or more biologically active agents to a tissue, wherein the medicament comprises one or more biologically active agents.

In another aspect the invention provides the use of (a) an aqueous solution of an dicarboxy-derivatized chitosan polymer and (b) an aqueous solution of an aldehyde-derivatized dextran polymer in the manufacture of a medicament for delivering one or more biologically active agents to a tissue, wherein (a) and (b) combine to form a hydrogel of the invention and wherein one or both of (a) and (b) include one or more biologically active agents.

In the methods and uses of the invention described above:

In one embodiment the hydrogel forms within about 1 sec to about 5 minutes of combining (a) and (b) to produce the medicament.

In one embodiment the hydrogel forms within about 1 sec to about 30 sec, preferably within about 1 sec to about 20 sec, more preferably within about 1 sec to about 10 sec. In another embodiment the hydrogel forms within about 30 sec to about 5 minutes. In another embodiment, the hydrogel forms within about 5 sec to about 1 min.

In one embodiment the hydrogel forms within about 5 minutes to about 20 minutes of combining (a) and (b) to produce the medicament.

In one embodiment the hydrogel forms within about 5 minutes to about 10 minutes. In another embodiment the hydrogel forms within about 10 minutes to about 20 minutes.

In one embodiment the hydrogel forms within about 20 minutes to about 2 hours of combining (a) and (b) to produce the medicament.

In one embodiment the hydrogel forms within about 30 minutes to about 2 hours, preferably within about 30 minutes to about 1 hour.

In one embodiment (a) comprises between about 2% to about 10% w/v dicarboxy-derivatized chitosan polymer, preferably between about 2% to about 8% w/v, more preferably about 5% w/v. In one embodiment (b) comprises between about 2% to about 10% w/v aldehyde-derivatized dextran polymer, preferably between about 2% to about 8% w/v, more preferably about 5% w/v.

In one embodiment (a) has a pH of between about 6 to 8, preferably between about 6.5 to 7.5.

In one embodiment (b) has a pH of between about 6 to 8, preferably between about 6.5 to 7.5.

In one embodiment the dicarboxy-derivatized chitosan is N-succinyl chitosan.

In another aspect the invention provides a wound dressing capable of releasing a hydrogel of the invention when moistened.

In one embodiment the wound dressing comprises a dicarboxy-derivatized chitosan polymer and an aldehyde-derivatized dextran polymer. In one embodiment the dicarboxy-derivatized chitosan polymer is N-succinyl chitosan.

In one embodiment the wound dressing is selected from the group comprising a bandage, strip, pad, gauze, film, stocking and tape.

In another aspect the invention provides a kit for use in the methods of the invention wherein the kit comprises:

(a) a dicarboxyl-derivatized chitosan polymer, and
(b) an aldehyde-derivatized dextran polymer.

In one embodiment the kit also comprises an aqueous solution in which (a) and (b) can be dissolved to allow cross-linking to occur. In another embodiment, the kit also comprises an aqueous solution of either or both of (a) and (b).

In another aspect the invention provides a kit for use in the methods of the invention wherein the kit comprises in separate containers:

(a) a dicarboxyl-derivatized chitosan polymer, and
(b) an aldehyde-derivatized dextran polymer.

In one embodiment the kit also comprises an aqueous solution in which (a) and (b) can be dissolved to allow cross-linking to occur. In another embodiment, the kit also comprises an aqueous solution of either or both of (a) and (b).

In the kits of the invention described above:

In one embodiment the kit of the invention also comprises instructions for use in a method of preventing or reducing post-surgical adhesion of tissue that is susceptible to adhesion formation.

In one embodiment the kit of the invention also comprises instructions for use in a method of accelerating or promoting wound healing.

In one embodiment the kit of the invention also comprises instructions for use in a method of reducing or stopping bleeding of a wound.

In one embodiment, the dicarboxyl-derivatized chitosan polymer and the aldehyde-derivatized dextran polymer provided in the kit of the invention are freeze-dried. In one embodiment the kit also comprises an aqueous solution in which to dissolve the dicarboxyl-derivatized chitosan polymer and the aldehyde-derivatized dextran polymer.

In one embodiment, at least one of, preferably both of the dicarboxyl-derivatized chitosan polymer and the aldehyde-derivatized dextran polymer are separately provided in an aqueous solution. In one embodiment the aqueous solutions are frozen.

In one embodiment the aqueous solution of dicarboxy-derivatized chitosan polymer comprises between about 2% to about 10% w/v of a dicarboxy-derivatized chitosan polymer. Preferably, the aqueous solution comprises between about 2% to about 8% w/v, more preferably about 5% w/v of a dicarboxy-derivatized chitosan polymer.

In one embodiment the aqueous solution of dicarboxy-derivatized chitosan polymer has a pH of between about 6 to 8. Preferably, the aqueous solution of dicarboxy-derivatized polymer has a pH between about 6.5 to 7.5.

In one embodiment the dicarboxy-derivatized chitosan is N-succinyl chitosan.

In one embodiment the aqueous solution of aldehyde-derivatized dextran polymer comprises between about 2% to about 10% w/v of an aldehyde-derivatized dextran polymer. Preferably, the aqueous solution comprises between about 2% to about 8% w/v, more preferably, about 5% w/v of an aldehyde-derivatized dextran polymer.

In one embodiment the aqueous solution of aldehyde-derivatized dextran polymer has a pH of between about 6 to 8. Preferably, the aqueous solution of aldehyde-derivatized dextran has a pH of between about 6.5 to 7.5.

Optionally, either or both of the aqueous solutions may contain one or more pharmaceutically acceptable excipients.

In one embodiment, the aqueous solution is selected from the group comprising water, saline, buffer and mixtures thereof. Preferably, the aqueous solution is about 0.9% w/v saline solution.

In one embodiment either or both of the aqueous solutions may contain one or more biologically active agents and/or one or more non-biologically active agents.

In one embodiment one or more of (a) and (b) also incorporates one or more biological active agents.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

DETAILED DESCRIPTION OF THE INVENTION

1. Definitions

Figure 1:
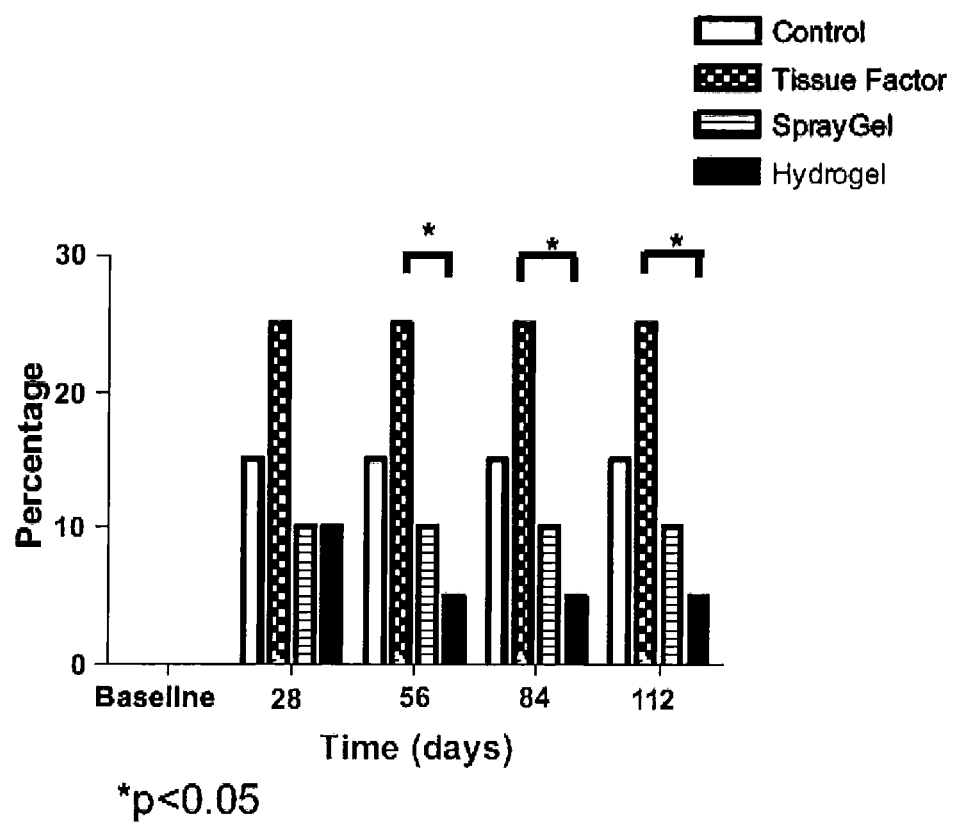
FIG. 1 is a graph showing the percentage of sheep in each group of the trial described in Example 6 with adhesions on the lateral nasal wall following treatment.

As used herein the term "chitosan" means a linear polysaccharide composed of randomly distributed β-(1,4) linked D-glucosamine and N-acetyl-D-glucosamine. Chitosan can be produced by deacetylation of chitin. Both α- and β-chitosan are suitable for use in the invention. The degree of deacetylation (% DA) influences the solubility and other properties of the chitosan. Commercially available chitosan typically has a degree of deacetylation of between about 50 to 100%. A monomer unit of fully deacetylated chitosan is shown in formula I below.

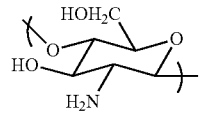

I

As used herein the term "dicarboxy-derivatized chitosan polymer" means a chitosan polymer that has been derivatized by reaction of a cyclic anhydride with the amine group of some of the D-glucosamine residues of the chitosan polymer. Examples of dicarboxy groups include N-succinyl, N-maloyl and N-phthaloyl. N-succinyl is preferred.

The "dicarboxy-derivatized chitosan polymer" may also be partially derivatized with other functional groups. This secondary derivatization can occur either at amine positions that are not derivatized with a dicarboxy group or at the hydroxy groups of the D-glucosamine residues. For example, reaction of the cyclic anhydride with an OH group of the chitosan may lead to some monomers containing ester groups rather than, or in addition to the amide substituent.

If secondary derivatization is present at the amine position of the dicarboxy-derivatized chitosan polymer, the polymer must retain sufficient free amine groups to be able to form cross-links with the aldehyde-derivatized dextran polymer. Preferably, the dicarboxy-derivatized chitosan polymer is only derivatized by reaction of the cyclic anhydride with the amine group of some of the D-glucosamine residues.

As used herein the term "N-succinyl chitosan polymer" means chitosan that has been derivatized by addition of an N-succinyl group on the amine group of some of the D-glucosamine residues of the chitosan polymer. A monomer unit of an N-succinyl chitosan polymer is shown in formula II below.

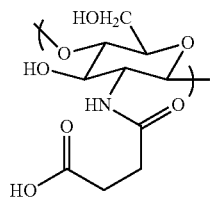

II

The degree of succinylation may vary. Typically, it is between about 30 to 70%, but the N-succinyl chitosan polymer must retain sufficient free amine groups to be able to form cross-links with the aldehyde-derivatized dextran. The N-succinyl chitosan polymer may also include secondary derivatization as discussed for the "dicarboxy-derivatized chitosan polymer" (above).

The term "N-succinyl chitosan" as used herein, means an N-succinyl chitosan polymer that is only derivatized with N-succinyl groups at the amine positions and does not include secondary derivatization with other functional groups.

As used herein the term "dextran" means a glucose polysaccharide composed of α-(1,6) glycosidic linkages with short α-(1,3) side chains. A monomer unit of dextran is shown in formula III below.

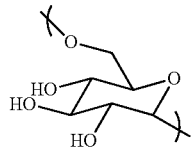

III

Dextran can be obtained by fermentation of sucrose-containing media by Leuconostoc mesenteroides B512F. Dextrans of molecular weights from 1 kDa to 2000 kDa are commercially available.

As used herein the term "aldehyde-derivatized dextran polymer" means a dextran polymer in which some vicinal secondary alcohol groups have been oxidised to give a reactive bisaldehyde functionality. Aldehyde-derivatized dextran polymers may also be derivatized at other positions with other functional groups. Preferably, the aldehyde-derivatized dextran polymer is only derivatized at vicinal secondary alcohol groups. A representative monomer unit of aldehyde-derivatized dextran polymer is shown in formula IV below.

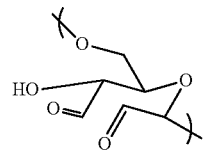

IV

As used herein the term "controlled release" in the context of controlled release of a biologically active agent means longer than expected delivery of a biologically active agent compared to what would be expected based on diffusion only.

As used herein the term "hydrogel" means a two- or multicomponent system consisting of a three-dimensional network of polymer chains and water that fills the spaces between the macromolecules.

As used herein the term "tissue" means an aggregate of morphologically similar cells with associated intercellular matter that acts together to perform one or more specific functions in the body of an organism including a human. Examples of tissues include but are not limited to muscle, epidermal, nerve and connective tissue.

The term "tissue" also encompasses organs comprising one or more tissue types including but not limited to the chest tissues such as the aorta, the heart, the pleural cavity, the trachea, the lungs, the pericardium and pericardial cavity; the abdominal and retroperitoneal tissues such as the stomach, the small and large intestines, the liver, the pancreas, the gall bladder, the kidneys and the adrenal glands; pelvic cavity tissues including the tissues of the male and female reproductive and urinary tracts; central and peripheral nervous system tissues such as the spinal column and nerves, dura and peripheral nerves; musculoskeletal system tissues such as skeletal muscle, tendons, bones and cartilage; head and neck tissues such as the eye, ear, neck, larynx, nose and paranasal sinuses.

As used herein the term "adhesion" means an abnormal attachment between tissues or organs or between tissues and implants that form after an inflammatory stimulus, such as surgery.

Tissues that are susceptible to adhesion formation are tissues that have been exposed to an inflammatory stimulus. For example, tissues which have been involved in surgical procedures such as but not limited to endoscopic sinus surgery, abdominal surgery, gynaecological surgery, musculoskeletal surgery, ophthalmic surgery, orthopaedic surgery and cardiovascular surgery. Tissues may also be susceptible to adhesion formation following other events such as mechanical injury, disease, for example, pelvic inflammatory disease, radiation treatment and the presence of foreign material, for example, a surgical implant.

As used herein the term "wound" means any damage to a tissue in a living organism including human organisms. The tissue may be an internal tissue such as an internal organ or an external tissue such as the skin. The damage may have resulted from a surgical incision or the unintended application of force to the tissue. Wounds include damage caused by mechanical injuries such as abrasions, lacerations, penetrations and the like, as well as burns and chemical injuries. The damage may also have arisen gradually such as occurs in an ulcer, lesion, sore, or infection. Examples of wounds include, but are not limited to, contused wounds, incised wounds, penetrating wounds, perforating wounds, puncture wounds and subcutaneous wounds.

As used herein the term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

2. The Polymer Network

The invention relates to a novel polymer network formed by derivatization and cross-linking of two well-known polymers; chitosan and dextran. The polymer rapidly forms a three-dimensional polymer network, creating a hydrogel in aqueous solution. The properties of the hydrogel can be tailored for specific applications by modifying the derivatization and cross-linking of the two polymer components.

In its broadest aspect the invention provides a polymer network comprising a dicarboxy-derivatized chitosan cross-linked to an aldehyde-derivatized dextran.

2.1 The Chitosan Component

Chitosan is widely available and can be obtained commercially from a range of sources, for example, Sigma-Aldrich (www.sigma-aldrich.com).

Alternatively, chitosan can be prepared by deacetylation of chitin. Many deacetylation methods are known in the art, for example, hydrolysing chitin in a concentrated solution of sodium hydroxide on heating and then recovering chitosan by filtering and washing with water. Chitin exists as either α-chitin or β-chitin, depending on whether the linkage between the glucosamine units is α or β. Chitin is found in crustaceans, insets, fungi, algae and yeasts. α-chitin is obtained predominantly from the shells of crustaceans such as lobster, crab and shrimp, whereas β-chitin is derived from squid pens. Both types of chitin can be used to prepare the dicarboxy-derivatized chitosan for use in the invention.

Generally, the average molecular weight ($MW_{av}$) of commercially available chitosan is between about 1 to 1000 kDa. Low molecular weight chitosan has a $MW_{av}$ of about 1 to 50 kDa. High molecular weight chitosan has a $MW_{av}$ of about 250 to 800 kDa. Chitosan of any $MW_{av}$, can be used in the invention.

Deacetylation of chitin means that the resulting chitosan has a majority of free, primary amine groups along its polymeric backbone. The degree of deacylation of the chitosan may influence the properties of the polymer network of the invention because only those glucosamine units that are deacetylated are available for derivatization or cross-linking. In addition, the solubility of the chitosan depends on the degree of deacylation.

Chitosan polymers most suitable for use in the invention have a degree of deacetylation of between about 40% to 100%. Preferably, the degree of deacylation is between about 60% to 95%, more preferably, between about 70% to 95%.

Chitosans for use in the invention are dicarboxy-derivatized at the amine made free by deacetylation of the chitin. Dicarboxy-derivatized chitosan polymers can be made by reacting chitosan with a cyclic acid anhydride. Cyclic acid anhydrides suitable for use in the invention include succinic anhydride, maleic anhydride, phthalic anhydride, glutaric anhydride, citraconic anhydride, methylglutaconic anhydride, methylsuccinic anhydride and the like.

Preferably, the dicarboxy-derivatized chitosan polymer is made from the reaction of chitosan and one or more of succinyl anhydride, phthalic anhydride, or glutaric anhydride. More preferably, the dicarboxy-derivatized chitosan polymer is made from the reaction of chitosan and succinyl anhydride.

Derivatization can be achieved by any method known in the art. For example, the solid chitosan can be heated in a solution of cyclic anhydride in DMF or solubilised in a methanol/water mixture and then reacted with the anhydride. Other solvents suitable for use in the derivatization process include dimethylacetamide. Acids such as lactic acid, HCl or acetic acid can be added to improve the solubility of the chitosan. A base such as NaOH is typically added to deacetylylate some of the acetylated amine groups.

Typical methods are provided in Example 1. The method used can be selected depending on the cyclic anhydride used and/or the average molecular weight of the chitosan. Both the chitosan and the cyclic anhydride should be able to substantially dissolve or swell in the solvent used.

In a preferred embodiment, the dicarboxy-derivatized chitosan is N-succinyl chitosan. Methods of preparing N-succinyl chitosan are well known in the art. See for example, "Preparation of N-succinyl chitosan and their physical-chemical properties", *J Pharm Pharmacol.* 2006, 58, 1177-1181.

The reaction of the cyclic anhydride with the chitosan acylates some of the free amine positions with dicarboxy groups. For example, when the cyclic anhydride used is succinic anhydride, some of the amine groups are N-succinylated. The NaOH treatment following N-succinylation removes some of the acyl groups from the amine groups in the chitosan. Increasing the temperature of the NaOH treatment increases the percentage of free amine groups present, as demonstrated in Example 4.

The degree of acylation is indicated by the ratio of C:N in the product. The degree of acylation can also be determined by $^1$H NMR. An N-succinyl chitosan polymer is represented below. Formula V shows the three types of D-glucosamine units present in the polymer—the N-succinylated-D-glucosamine, the free D-glucosamine, and the N-acetyl-D-glucosamine.

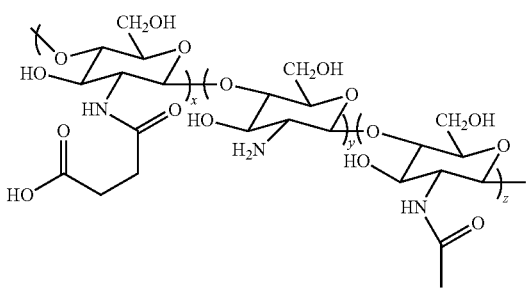

V

In one embodiment, x is between about 60 to 80%, y is between about 1 to 15% and z is between about 10 to 25%.

In another embodiment, x is between about 60 to 80%, y is between about 1 to 30% and z and between about 2 to 25%.

High degrees of anhydride substitution render the dicarboxy-derivatized chitosan polymer more soluble but may hinder cross-linking to the aldehyde-derivatized dextran polymer.

In one embodiment, the dicarboxy-derivatized chitosan polymer is between about 20% and 80% dicarboxy derivatized. Preferably, the dicarboxy-derivatized chitosan polymer is between about 30% and 60% dicarboxy derivatized. More preferably, dicarboxy-derivatized chitosan polymer is between about 45% and 50% dicarboxy derivatized.

In one embodiment, the dicarboxy-derivatized chitosan polymer is between about 50% and 90% dicarboxy derivatized. Preferably, the dicarboxy-derivatized chitosan polymer is between about 60% and 80% dicarboxy derivatized.

2.2 The Dextran Component

Dextran is a polysaccharide made of D-glucose units linked predominantly by a-1,6 linkages. Crude, high molecular weight dextran is commercially obtained by growing *Leuconostoc mesenteroies* on sucrose. The resulting polysaccharide is hydrolysed to yield low molecular weight dextrans.

Before dextran can be cross-linked to the dicarboxy-derivatized chitosan polymer, it must be activated. Reactive bisaldehyde functionalities can be generated from the vicinal secondary alcohol groups on dextran by oxidation. Typical methods are provided in Example 2. The resulting aldehyde-derivatized dextran polymer can then be reductively coupled to the primary amine groups of the dicarboxy-derivatized chitosan to form a cross-linked polymer network of the invention.

In one embodiment, the oxidising agent is sodium periodate. Other suitable oxidising agents include potassium periodate and the like.

The oxidised product, the aldehyde-derivatized dextran polymer, actually only contains a small amount of free aldehyde groups. Most of the aldehyde groups are masked as acetals and hemiacetals, which are in equilibrium with the free aldehyde form of the dextran.

Reaction of some of the free aldehyde groups causes the equilibrium to shift from the acetal and hemiacetal form, towards the formation of more free aldehyde groups.

The degree of oxidation can be influenced by the molar ratio of oxidising agent used. A higher degree of oxidation will provide an aldehyde-derivatized dextran polymer with more sites available for cross-linking. However, a lower degree of oxidation will result in a more soluble aldehyde-derivatized dextran polymer. The periodate reaction also dramatically decreases the molecular weight of the dextran polymer.

In one embodiment, the degree of oxidation is between about 30% to about 100%, more preferably between about 50% to about 100%. Most preferably, the degree of oxidation is between about 80 to about 100%.

Example 5 compares gelling times for polymer networks of the invention prepared using aldehyde-derivatized dextran polymers with different degrees of aldehyde-derivatization (or oxidation). More highly aldehyde-derivatized dextran polymers have lower molecular weights and form gels faster, when combined in solution with solutions of N-succinyl chitosan.

The degree of derivatization can be measured using the extended reaction with hydroxylamine hydrochloride and then titration of the liberated protons (Zhao, Huiru, Heindel, Ned D, "Determination of degree of substitution of formyl groups in polyaldehyde dextran by the hydroxylamine hydrochloride method," *Pharmaceutical Research* (1991), 8, page 400-401).

2.3 Cross-linking the Chitosan Component with the Dextran Component

The invention provides a polymer network comprising a dicarboxy-derivatized chitosan polymer cross-linked to an aldehyde-derivatized dextran polymer. In one embodiment the dicarboxy-derivatized chitosan polymer is an N-succinyl chitosan polymer. In one embodiment the N-succinyl chitosan polymer is cross-linked to the aldehyde-derivatized dextran polymer through the amine group of the N-succinyl chitosan polymer and the aldehyde group of the aldehyde-derivatized dextran polymer. Preferably, the N-succinyl chitosan polymer is N-succinyl chitosan.

The invention also provides a method of producing a polymer network as described above.

To make a polymer network of the invention, the dicarboxy-derivatized chitosan polymer is cross-linked to the aldehyde-derivatized dextran polymer. This can be achieved by mixing aqueous solutions of the two polymers. For example, see Example 3.

Once made, aqueous solutions of each polymer component can either remain in solution, or can be dried, for example by freeze-drying, to product a solid product. The solid polymer components can then be redissolved in aqueous solution before being mixed together to form the hydrogel of the invention.

In one embodiment, it is desirable that the aqueous solution in which the polymer matrix forms has a pH of about 6 to 8, preferably between about 6.5 to 7.5. This can be achieved by adjusting the pH of the separate aqueous solutions of the polymer components to within this range before mixing the two solutions. Alternatively, the pH of the aqueous solutions of the individual polymer components can be adjusted following dialysis, prior to freeze drying. The pH can be adjusted using any suitable base or acid. Generally, the pH will be adjusted using NaOH.

In one embodiment either or both of the aqueous solutions may independently contain one or more pharmaceutically acceptable excipients. In one embodiment the aqueous solutions may independently contain NaCl. Preferably, the concentration of NaCl is between about 0.5 to 5% w/v. More preferably, the concentration of NaCl is between about 0.5% to 2% w/v, most preferably about 0.9% w/v.

In one embodiment the aqueous solutions may independently contain one or more buffers including but not limited to phosphate buffers such as $Na_2HPO_4$, acetate buffers, carbonate buffers, lactate buffers, citrate buffers and bicarbonate buffers.

2.4 The Hydrogels of the Invention

The dicarboxy-derivatized chitosan polymer reacts with the aldehyde-derivative dextran polymer, to produce a three-dimensional cross-linked polymer network. This polymer network forms a hydrogel with the aqueous solution in which it is formed. The hydrogel of the invention has properties that make it suitable for use in medicinal applications, in particular, wound healing, prevention of surgical adhesions, and reducing bleeding (haemostasis).

Without being bound by theory, it is believed that application of the hydrogel of the invention to a wound surface prevents the formation of fibrin and blood clots within this space thereby preventing subsequent formation of adhesions.

The properties of the hydrogel can be tailored for specific applications by modifying the derivatization and cross-linking of the two polymers.

In the polymer networks of the invention, the amine groups of the D-glucosamine residues of chitosan may be
 (a) cross-linked to the aldehyde-derivatized dextran polymer,
 (b) acylated with a dicarboxy group, or
 (c) acetylated (from the original chitin material).

High degrees of acetylation and/or dicarboxy acylation will leave less free amine groups to cross-link with the aldehyde-derivatized dextran polymer. Consequently, when the aqueous solutions of the two polymers are mixed, the amount of polymerisation that occurs will be affected by the acylation and acetylation patterns of the dicarboxy-derivatized chitosan polymer. This in turn will affect how quickly, if at all, the hydrogel is formed. If very little polymerisation occurs in a dilute solution of the polymers, no hydrogel will be formed.

The aqueous solutions of dicarboxy-derivatized chitosan polymer and aldehyde-derivatized dextran polymer comprise between about 2% to about 10% w/v of each component.

Generally, aqueous solutions of equal concentrations of the two polymers are mixed to form the hydrogel of the invention. However, different ratios of dicarboxy-derivatized chitosan polymer and aldehyde-derivatized dextran polymer can be used, provided the properties of the two polymers are such that they cross-link to form a hydrogel of the invention when mixed together.

A person skilled in the art can manipulate the parameters of
 (a) degree of deacetylation of chitosan,
 (b) degree of dicarboxy-derivatization of chitosan,
 (c) degree of oxidation of aldehyde-derivatized dextran, and
 (d) concentration in aqueous solution, so that the component polymer solutions rapidly cross-link to form a hydrogel when mixed.

Alternatively, the person skilled in the art can manipulate these parameters to ensure that the hydrogel forms slowly, or within a given time period, if this is desirable.

Factors such as secondary derivatization of the polymers, the nature of the aqueous solutions and the addition of biologically active or non-biologically active agents should also be taken into consideration. For example, a hydrogel of the invention may form more rapidly when the pH of the aqueous solution comprising the mixed polymer components is between about 6 to 8.

Using the methods described herein by manipulating the parameters discussed above, the inventors have made hydrogels of the invention that form within a second or two of mixing the solutions of the polymer components. Other hydrogels of the invention form over a period of minutes, or even hours once the two solutions have been mixed.

The dicarboxy-derivatized chitosan polymer and aldehyde-derivatized dextran polymer solutions may be sterilised before use, to ensure their application to a tissue does not introduce microorganisms into the tissue. Alternatively, the freeze-dried solid dicarboxy-derivatized chitosan polymer and aldehyde-derivatized dextran polymer can be sterilised then dissolved in sterilised aqueous solutions.

The solutions can be sterilised using any technique known in the art. For example, by radiation sterilization using gamma rays from a radioisotope source (usually cobalt-60), or electron beam or x-ray irradiation.

Exposure to radiation may cause chemical changes that can affect the functioning of the dicarboxy-derivatized chitosan and aldehyde-derivatized dextran polymers. For example, if free amine groups are oxidised, less will be available for cross-linking between the polymer components and it may take longer for a gel to form. Radiation may also decrease the molecular weight of the polymer components. These factors should be taken into account when preparing dicarboxy-derivatized chitosan and aldehyde-derivatized dextran components that are intended to form a hydrogel in a certain time frame when mixed together in solution.

The hydrogel of the invention can also contain one or more biologically active agents, and/or one or more non-biologically active agents.

In one embodiment the one or more biologically active agents are selected from the group comprising plasma proteins, hormones, enzymes, antibiotics, antiseptic agents, antineoplastic agents, antifungal agents, antiviral agents, anti-inflammatory agents, growth factors, steroids, cell suspensions, cytotoxins, and cell proliferation inhibitors.

Biologically active agents incorporated into the hydrogel matrix will be released when the hydrogel breaks down. In this way, the hydrogel of the invention can be used to deliver biologically active agents to a target area.

Non-biologically active agents can also be incorporated into the hydrogel matrix. For example, polysaccharide thickeners such as hydroxyethyl cellulose, carboxymethyl cellulose, guar gum, locust bean gum, xanthan gum and the like, or polymer thickeners such as polyacrylic acids and copolymers, polyacrylamides and copolymers, alcohols, maleic anhydride copolymers and the like can be added to produce a stiffer hydrogel.

Polysaccharide thickeners may also be added to the aqueous solutions of the polymer components to ensure that the solutions are of suitable viscosity for application. For example, if the hydrogel is to be formed in situ on a target area such as a wound or tissue, the aqueous solutions of the polymer components should be sufficiently viscous that they do not drain away from before cross-linking can occur. Therefore, if the particular dicarboxy-derivatized chitosan polymer and/or aldehyde-derivatized dextran polymer used form very non-viscous aqueous solutions, a thickener may be used to increase the viscosity. In other embodiments, the aqueous solutions of the polymer components will be sufficiently viscous without the addition of a thickener.

Similarly, dyes such as fluorescein and methylene blue can be incorporated into the hydrogel matrix so that the precise location and amount of the hydrogel applied can be ascertained.

These additional agents can be incorporated into the hydrogel by any method known in the art. For example, if the agent is a solid substance it can be blended with one of the dried polymer components. The combined dried material is then dissolved in the aqueous solution which is then mixed with the aqueous solution of the second polymer component.

If the agent to be incorporated is a liquid, it can be directly combined with one of the aqueous polymer solutions and then freeze dried for storage. Alternatively, it can be added directly to the mixture of aqueous polymer solutions before the solutions are mixed to form the hydrogel of the invention.

It is also possible for an agent to covalently react with one of the polymer components. If large amounts of agent are present and an agent reacts with the free amine groups of the N-succinyl chitosan, the resulting hydrogel may take longer to form. However, any covalent reaction between the agent and the polymer components must prevent cross-linking to the extent that the hydrogel cannot form.

When the hydrogel degrades, the agent will be hydrolysed from the polymer.

3. Using the Hydrogels of the Invention

In one aspect the invention provides a method of preventing or reducing adhesion of tissue susceptible to adhesion formation comprising treating the tissue with a hydrogel of the invention.

In one embodiment the adhesion is post-surgical adhesion.

In another aspect the invention provides a method of reducing or stopping bleeding of a wound comprising treating the wound with a hydrogel of the invention.

In one aspect the invention provides a method of accelerating or promoting wound healing comprising treating the wound with a hydrogel of the invention.

For the methods of the invention described above:

In one embodiment the hydrogels of the invention are produced in situ. Aqueous solutions of the dicarboxy-derivatized chitosan polymer and aldehyde-derivatized dextran polymer can be simultaneously applied by, for example, spraying, squirting or pouring the solutions onto the target area. The target area may be a wound, in particular a surgical wound, or a tissue.

The two components meet and mix in the air, or on the surface of the wound or tissue and react to produce a cross-linked polymer network. Formation of the polymer network in aqueous solution creates a hydrogel.

The solutions can be sprayed, squirted or poured onto the target area using any means known in the art. When sprayed, the aqueous solutions are simultaneously expelled from separate containers in a mass of dispersed droplets. The containers may be pressured. For example, PCT publication WO 00/09199 describes an apparatus that permits spraying of two polymerizable fluids. The apparatus sprays fluids stored in separate chambers so that the fluids mix only in the emergent spray.

When squirted, the polymer-containing aqueous solutions are simultaneously ejected from separate containers in a liquid stream. For example, the aqueous solutions can be squirted onto a target area using separate syringes and an applicator that allows the solutions to mix at its tip as they are being applied to the target area. Alternatively, the solutions can be simply poured onto the target area.

The two polymer solutions should be applied simultaneously but need not reach the target area in exactly the same quantities at exactly the same time, provided that sufficient cross-linking occurs to form a hydrogel.

The various methodologies and devices for performing in situ gelation developed for other adhesive or sealant systems may be used to apply the aqueous solutions of polymer to form the hydrogel of the invention.

In another embodiment the hydrogel of the invention is used by first mixing the dicarboxy-derivatized chitosan polymer with the aldehyde-derivatized dextran polymer to form the polymer network in aqueous solution and then applying the hydrogel that forms to the area to be treated. The time taken between mixing the polymers and applying the hydrogel depends on the speed at which the gel forms. Any method known in the art can be used to apply the hydrogel to the target area. For example, the hydrogel can be applied using a wide-bore syringe.

In one embodiment, the amount of hydrogel used should be sufficient to (a) reduce or minimise the number of adhesions in the treatment area, (b) accelerate or promote healing of the wound to which it is applied, or (c) reduce or stop bleeding of the wound to which it is applied.

While the hydrogels of the invention can be used to reduce or minimise tissue adhesions caused by any adhesion-forming event, they are particularly useful for preventing or reducing post-surgical adhesions.

The methods of the invention can be applied to treat any organism. In one embodiment, the methods are applied to humans.

The ability of the hydrogels to reduce both bleeding and adhesions, makes them a valuable tool in practically any surgical procedure. Examples of surgical procedures in which the hydrogels of the invention can be used include but are not limited to abdominal procedures such as bowel surgery, thoracic procedures, neurosurgical procedures including intercranial and spinal surgery, nerve releasing procedures and procedures on the lining of the brain, pelvic procedures such as ovarian cystectomy and hysterectomy, sinus surgery, ophthalmic procedures, otologic procedures, neck and laryngeal procedures such as vocal fold and cord procedures, orthopaedic procedures such as division of adhesions on flexor and extensor tendons and burns procedures.

The hydrogel of the invention is particularly suited for use in ear, nose and throat surgery. A weakness of gel formation in sinuses is that mucociliary clearance will slowly clear gels from the surface of the sinus. The ciliary beating of the nasal mucociliary clearance system acts to transport the mucus layer that covers the nasal epithelium towards the nasopharynx. In doing so, any substances applied to the surface of the sinuses will be similarly expelled. The hydrogels of the invention become quite firm soon after application and therefore resist being cleared away by the nasal mucociliary clearance system. Once applied, the hydrogel of the invention maintains a physical barrier between internal tissues to prevent adhesions. As the tissue surfaces heal, the hydrogel degrades and is eliminated from the site.

The hydrogels of the invention can also be applied to dermatological and cutaneous wounds, either directly, or by using a wound dressing incorporating the hydrogel.

3.1 Delivery of Biologically Active Agents Using the Hydrogels of the Invention The hydrogels of the invention can be used as site-directed controlled release carriers for biologically active agents. Accordingly, one aspect the invention provides a method of delivering one or more biologically active agents to a tissue comprising treating the tissue with a hydrogel of the invention wherein the hydrogel contains one or more biologically active agents.

Site-directed delivery of the biologically active agent can reduce the side-effects associated with conventional systemic administration and ensure that a therapeutically effective amount of the biologically active agent reaches the affected area. For example, the polymer network of the invention can be used to treat chronic venous insufficiency and leg ulcers. Pro-angiogenic and epithelial growth factors incorporated into the polymer network can assist in healing ulcers. The polymer network of the invention may be applied directly to the wound as a gel, or incorporated into a wound healing dressing, for application to the wound.

Biologically active agents that can be incorporated into the polymer network of the invention include but are not limited to plasma proteins, hormones, enzymes, antibiotics, antiseptic agents, antineoplastic agents, antifungal agents, antiviral agents, anti inflammatory agents, growth factors, anaesthetics, steroids, cell suspensions, cytotoxins and cell proliferation inhibitors.

The biologically active agent may act in conjunction with the polymer of the invention to contribute to wound healing. For example, antibiotics such as tetracycline, ciprofloxacin and the like; growth factors such as heparin binding growth factors, including the fibroblast growth factors; platelet-derived growth factors, insulin-binding growth factor-1, insulin-binding growth factor-2, epidermal growth factor, transforming growth factor-alpha, transforming growth factor-beta, platelet factor 4 and heparin binding factors 1 and 2, can all be incorporated into the polymer network of the invention.

Other biologically active agents that can be used include but are not limited to antifungal agents such as nystatin, diflucan, ketaconizole and the like; antivirals such as gangcyclovir, zidovudine, amantidine, vidarabine, ribaravin, trifluridine, acyclovir, didexoyuridine and the like; anti-inflammatory agents such as alpha-1-antitrypsin, alpha-1-antichymotrypsin and the like; cytotoxins or cell proliferation inhibitors such as 5-fluorouracil, taxol, taxotere, actinomycin D, andriamycin, azaribine, bleomycin, busulfan, butyric acid, carmustine, chlorambucil, cis-platin, cytarabine, cytarabine, dacarbazine, estrogen, lomustine, emlphalan, mercaptopurine, methotrexate, mitomycin C, prednisilone, prednisone, procarbazine, streptozotocin, thioguanine, thiotepa, tributyrin, vinblastine, vincristine, gentamycin, carboplatin, cyclophosphamide, ifosphamide, maphosphamide, retinoic acid, ricin, diphtheria toxin, venoms and the like; hormones such as estrogen, testosterone, insulin and the like; steroids such as beclomethasone, betamethasone, budesonide, cortisone, dexamethasone, fluticasone, hyudrocortisone, methyl-prednisolone, memetasone, prednisone/prednisolone, triamcinolone and the like; plasma proteins such as albumin; immunoglobulins, including immunoglobulin A, M and G; fibrinogen; coagulation factors, including Factors II, VII, VIII, IX, X and XIII; lasmoinogen; protein C; protein S; plasma proteinase inhibitors, including anti-thrombin III, $\alpha$1-antitrypsin, $\alpha$2-macroglobulin, and C1 esterase inhibitor; $\alpha$1-acid glycoprotein; ceruloplasmin; haptoglobin; transferring; complement components C1 through C91 C4b binding protein; interalpha-trypsin inhibitor; apolipoproteins, including A-1, A-11, B, C and E; fibronectin and angiostatin.

The hydrogels of the invention may also include nutritional supplements such as peptides, proteins, simple carbohydrates, complex carbohydrates, lipids, glycolipids, glycoproteins, vitamins and minerals.

Incorporation of the biologically active agent into the hydrogels allows site-directed delivery of the agent. The rate of release can also be controlled by tailoring the degradation rate of the hydrogel.

The biologically active agent can be added to the hydrogel of the invention by any means known in the art. For example, by adding the agent to one polymer component solution before mixing the solutions together. The means of incorporation will depend on the nature of the biologically active agent.

The concentration of the biologically active agent to be added will vary depending on the nature of the agent, the site to which it is to be applied and the physical characteristics of the hydrogel. The concentration should be sufficient such that a therapeutically effective amount of the biologically active agent is delivered to the target site. In one embodiment the concentration of the biologically active agent is between about 1 ng/ml to about 1 mg/ml of the hydrogel. Preferably, the concentration of the biologically active agent is between about 1 ug/ml to about 100 ug/ml of the hydrogel. The appropriate amount of the biologically active agent to be added can be calculated by one of skill in the art by testing hydrogels containing various concentrations of biologically active agents and selecting the hydrogel that is most effective for the particular purpose.

The physical properties of the hydrogel of the invention ensure it will remain substantially in the same location as it is applied and will not quickly be flushed away by liquids in the body or sink due to gravity. The hydrogel will mould itself around the tissue to which it is applied, ensuring contact with the entire surface of the tissue.

4. Kits

In another aspect the invention provides a kit for use in the methods of the invention wherein the kit comprises:
 (a) a dicarboxyl-derivatized chitosan polymer, and
 (b) an aldehyde-derivatized dextran polymer.

The kits of the invention conveniently provide the polymer components that cross-link to form the hydrogel of the invention in aqueous solution.

In one embodiment the kits of the invention also comprise an aqueous solution into which polymers (a) and (b) can be dissolved to cross-link and form the hydrogel. Alternatively, the kits of the invention may provide (a) and/or (b) pre-dissolved in aqueous solution, ready for mixing with the second polymer component. The aqueous solutions can be provided in liquid or frozen form.

In one embodiment, the kits of the invention provide polymer components (a) and (b) as freeze-dried powders. To use the kits of the invention, the freeze-dried polymers are dissolved in a suitable aqueous solution and then mixed together. Alternatively, both (a) and (b) can be added to a suitable aqueous solution and mixed until dissolved and cross-linked. In one embodiment the aqueous solution is selected from the group comprising water, saline, buffer and mixtures thereof.

In one embodiment the kits of the invention may also comprise one or more biologically active agents. For example, the one or more biologically active agents can be incorporated into one or both of the polymer components (a) and (b). Alternatively, the one or more biologically active agents may be present in the aqueous solution in which (a) and/or (b) are to be dissolved.

5. Wound Dressings

The invention also provides wound dressings capable of releasing a hydrogel of the invention when moistened. The wound dressing can be any suitable dressing known in the art. Examples include bandages, strips, pads, gauzes, films, stockings and tape.

In one aspect the wound dressing comprises a dicarboxy-derivatized chitosan polymer and an aldehyde-derivatized dextran polymer. Preferably the dicarboxy-derivatized chitosan is N-succinyl chitosan.

To prepare a wound dressing of the invention, the dried solid dicarboxy-derivatized chitosan polymer and the aldehyde-derivatized dextran polymer are blended into the structure of the dressing. Alternatively, the wound dressing can be soaked in an aqueous solution of one polymer and then dried, with the second polymer being introduced as a matt. The matt can be held together by a third component, for example, a water soluble glue. As another alternative, the two polymers can be dried and mixed, then placed between two pieces of very porous tissue as part of the structure of the wound healing dressing.

When the wound dressing is moistened, the two polymer components cross-link and form a hydrogel in the aqueous component of the wound dressing. The wound dressing can be moistened either by external or internal fluids. For example, when placed on the wound the wound dressing may be moistened by contact with blood from the wound or wound exudate. If the wound is not sufficiently moist, the wound dressing can be moistened by contact with a suitable physiologically-acceptable liquid such as water or saline solution.

The rate at which the hydrogel forms can be altered by altering the component polymers. Different applications of the wound dressing may require different rates of hydrogel formation.

Pressure applied to the wound dressing may assist in hydrogel formation.

The wound dressing may contain additional agents such as antiseptics and other biologically active agents, as discussed above. These agents can be incorporated into the dressing materials using standard methods known in the art, or may be incorporated into the polymer solutions that are blended into the structure of the dressing.

Various aspects of the invention will now be illustrated in non-limiting ways be reference to the following examples.

EXAMPLES

Example 1

N-succinyl Chitosan Polymer (DMF Method)

Batch A. Succinic anhydride (2.15 g, 0.0215 mol) was added to chitosan (1.5 g, 0.007 mol) in 100 ml N,N-dimethylformamide (DMF). The mixture was heated to 150° C. under nitrogen for 3 hrs.

On cooling the solid was collected from the mixture and washed with methanol then acetone. The dried solid was dissolved in sodium hydroxide (400 ml, 2 M) and the solution stirred overnight. Not all of the solid dissolved. The undissolved solid was filtered and the solution evaporated to about 30-50 ml.

The solution was dialysed in a 3 L beaker by dialysis bag for 48-60 hours with the water changed periodically. The solution was then concentrated and freeze-dried. The N-succinyl-chitosan product was obtained as a cotton-like solid.

Batch B. Chitosan (from squid pens) (30 g) and succinic anhydride (42 g) in DMF (500 ml) was heated to 140° C. for 20 hrs. The resulting N-succinyl chitosan was recovered by filtration and washed with ethanol and then diethyl ether and dried at the pump. The dried solid was added to a solution of sodium hydroxide (10 g in 800 ml water) and stirred overnight. The solution was filtered through celite and dialysed for 3 days with the water changed every 12 hrs. Lyophilization produced 14 g of N-succinyl chitosan (analysed C 39.2%, H 5.9%, N 5.1%).

Batch C. Chitosan (30 g, practical grade Aldrich, medium molecular weight) and succinic anhydride (42 g) were heated to 130° C. in DMF (1 L) for 3 hours. The chitosan swelled but did not dissolve. On cooling the chitosan was filtered off, and washed with methanol on the filter. The chitosan was then added to a solution of NaOH (50 g in 1.5 L of water) and mixed with a high speed overhead stirrer until homogenous (usually 30 minutes). Occasionally the chitosan is not all soluble in which case any remaining gel is removed by filtration through celite. The solution was heated to 50° C. for 14 h and was dialysed in cellulose tubing for 3 days in distilled water (4 changes of 50 L). The pH was adjusted to 8.0 with a little sodium hydroxide. The solution was then reduced in volume to ca. 700 mL under reduced pressure on a rotary evaporator to give a very thick solution, and then freeze dried to yield ca. 35 g product.

N-succinyl Chitosan (Methanol Method)

Chitosan (Aldrich, practical grade) (20 g) was dissolved in lactic acid (20 ml) and water (650 ml) by stirring for 3 hr. Methanol (650 ml) was added and the mixture was warmed to 35° C. Succinic anhydride (29 g) was added and the mixture stirred vigorously for 4 hr at 35° C. The succinic anhydride took a few hours to dissolve. A solution of sodium hydroxide (35 g in 300 ml water) was added and the mixture stirred vigorously for 1 hr. The cloudy partially gelled mixture that resulted was dialysed for 1 day to remove the methanol, then vigorously stirred to break up the remaining final gel and dialysed in distilled water for a further 3 days (with a change of water every 12 hr) and filtered. Lyophilization gave the product (16.5 g).

Example 2

Aldehyde-derivatized Dextran

Batch A. Dextran (1 g, MW 60,000-90,000) was dissolved in 20 ml distilled water. Sodium periodate (2 g) was added to the solution which was stirred for 3 hours at room temperature. The solution was dialysed in a 3 L beaker overnight with the water changed periodically. The solution was then concentrated and freeze-dried to give aldehyde-derivatized dextran as a white powder.

Batch B. Dextran (20 g, Aldrich, Mn 21,500, MW 142,000) was dissolved in water (200 ml) and then added to a stirring mixture of sodium periodate (40 g in 200 ml). The temperature of the exothermic reaction was kept at below 35° C. by external cooling and the reaction was performed under nitrogen. After 3 hr, the solution was dialyzed for 3 days (water changed every 12 hr), filtered and lyophilized to give aldehyde-derivatized dextran as a white powder (14.7 g, found C 39.8%, H 5.9%). The final molecular weight was $M_n$ 2570, MW 4700.

Batch C. Dextran (36 g, Aldrich food grade, mw 80,000) was stirred vigorously in water (800 mL) while solid sodium periodate (50 g) was added. The exothermic reaction was controlled by external cooling so that the temperature stayed under 30° C. After 2 h the solution was filtered, and dialysed in cellulose tubing for 3 days (4 changes of 50 L distilled water). The pH was adjusted to 8.0 with a little sodium hydroxide, and the solution reduced in volume under reduced pressure to ca. 300 mL, and freeze dried. The yield was ca. 30 g.

Example 3

Polymer Network Comprising N-succinyl Chitosan Cross-linked with Aldehyde-derivatized Dextran Polymer in Aqueous Solution N-succinyl chitosan from Example 1 (30 mg) was dissolved in 0.6 ml distilled water to make a 5% w/v aqueous solution (Solution A). Aldehyde-derivatized dextran polymer (30 mg) was dissolved in 0.6 ml distilled water to make a 5% w/v aqueous solution (Solution B).

Solution A and Solution B were mixed together until a hydrogel formed (approximately 2 minutes). The hydrogel is the polymer network comprising N-succinyl-chitosan cross-linked with aldehyde-derivatized dextran polymer in aqueous solution.

Example 4

Effect of Base Treatment on Functional Group Levels of N-succinyl Chitosan and Gel Time of Hydrogel N-succinyl chitosan was prepared in accordance with Example 1 (DMF method-Batch C), but the solution of chitosan and NaOH was heated for 14 hours at the temperatures shown in Table 1 below. Table 1 shows that higher temperatures result in greater deacylation and hence a higher proportion of free amine groups. The relative properties of free amine groups to acetyl and N-succinyl groups was determined by $^1$H NMR.

Hydrogels prepared by cross-linking of the N-succinyl chitosan and aldehyde-derivatized dextran in accordance with Example 3 were formed faster where the N-succinyl chitosan has a higher proportion of free amines.

TABLE 1

Effect of base treatment on functional group levels of N-succinyl chitosan and gel formation of hydrogel time

| Temp | Mol % acetyl groups | Mol % succ groups | Mol % free amine | Gel time (s) |
|---|---|---|---|---|
| no base treatment | 16 | 93 | 0 | — |
| 35° C. | 15 | 91 | trace | — |
| 55° C. | 11 | 81 | 12 | 35 |
| 65° C. | 5 | 75 | 22 | 5 |

Example 5

Effect of mol % Periodate on Aldehyde Derivatization of Dextran and Gel Formation Time for Hydrogel Aldehyde-derivatized dextrans were prepared in accordance with Example 2, but different mol % of periodate were used. The reactions took place at room temperature for two hours. Table 2 shows the molecular weight of the resulting aldehyde-derivatized dextran, the mol % of aldehyde groups, and the time taken to form a hydrogel when a solution of the aldehyde-derivatized dextran is mixed with a solution of N-succinyl chitosan.

TABLE 2

| Mol % Periodate (2 h, rt) | MW dextran (Mn) | Mol % aldehyde groups | Gel time (s) |
|---|---|---|---|
| 0 | 95,500 | 0 | — |
| 26 | 20,270 | 32 | 220 |
| 52 | 14,059 | 75 | 70 |
| 78 | 10,010 | 118 | 45 |
| 105 | 3700 | 165 | 35 |

The theoretical maximum mol % of aldehyde groups present per chitosan residue is 200 which would be achieved if every mol of periodate reacted with one chitosan residue. A mol % of 200 represents 100% oxidation (or 100% aldehyde-derivatization).

Example 6

Effect of Hydrogel on Adhesions Following Endoscopic Sinus Surgery in Sheep

Standardised full thickness mucosal wounds were made in 20 sheep (merino cross wethers) using a well established endoscopic sinus surgery wound healing protocol. Each sheep was given two lateral nasal wall injuries and one ethmoidal injury on each side. The injured regions were randomized to 4 treatment groups and treated with one of (a) control (no treatment), (b) SprayGel™, (c) recombinant tissue factor, and (d) the hydrogel of the invention.

For groups (b), (c) and (d) 5 ml of active agent was sprayed onto the surface of the wound using a mucosal atomization device. SprayGel™ and the hydrogel of the invention were each sprayed as two separate liquid components which combined in the spray instantly to form a mucoadhesive gel.

The sheep were assessed at day 28, 56, 84 and 112. At each review the sheep were moderately sedated using an intramuscular injection of 4 mg xylazine. The nasal cavity was inspected at each of these 4 weekly visits with the presence of adhesions noted, their location recorded and each adhesion graded by an independent observer (animal lab technician) according to a previously published grading scheme (Table 3).

TABLE 3

Grading scheme for sheep nasal adhesions

| Grade 1 | Less than 25% of middle turbinate height |
| Grade 2 | 25-50% of middle turbinate height |
| Grade 3 | More than 50% of middle turbinate size |

Brushings of ciliated cells were collected from four regions in each sheep under endoscopic vision at a site distant from biopsy using a CYTOBRUSH PLUS™ cell collector (Medscand Medical, Sweden) without local anesthetic. Sites of brushings were carefully ordered and recorded during the 16 week period in order to sample untouched areas.

Four sprays of a combination anesthetic and decongestant spray (CO-PHENYLCAINE™—ENT technologies) were applied to each nasal cavity prior to biopsy of the lateral nasal wall injury sites. An incision was made and a small flap raised using a sharpened Freer elevator and two biopsy specimens taken from each injury site using punch biopsy forceps. Biopsies were taken at each four week interval with biopsy sites carefully ordered and recorded during the sixteen week period in order to sample untouched areas. Following the final biopsy, euthanasia was performed by intravenous injection of sodium pentobarbitone (>100 mg/kg).

Specimens for light microscopy were fixed in formalin for 4 hours, then placed in 70% ethanol and processed. Specimens were embedded in paraffin blocks, sectioned at 4 μm thickness and six to eight sections mounted on 2 glass slides for each biopsy specimen. They were then stained with Hematoxylin and Eosin (H&E). Each specimen was examined under light microscopy using image capture software (Image Master Pro). The percentage re-epithelialization was calculated by measuring the length of the nasal mucosal surface area with lamina propria and the length of this surface that had an epithelial covering. Four random sections were measured for each biopsy specimen. Epithelial height was also measured using these same digital images. Four random areas of epithelium from one section were measured for each specimen using the basement membrane and apical surface of the epithelium as markers.

Specimens for scanning electron microscopy (SEM) were placed in phosphate buffered saline and then washed for 20 minutes using an ultrasonic cleaner in order to remove blood clot, mucous, debris and biofilm. The specimens were then fixed in a solution of 4% paraformaldehyde/1.25% glutaraldehyde in phosphate buffered saline+4% sucrose, pH 7.2, and stored at 4° C. until processed. Processing involved progressive dehydration of the specimen using osmium tetraoxide, followed by increasing concentrations of ethanol (70&, 90%, 95%, 100% & 100%) using microwave technology (PELCO BIOWAVE™) for more rapid processing. After this the specimens were dried using a carbon dioxide critical point dryer and then mounted on EM stubs. Finally specimens were coated with gold and carbon. Each specimen was examined by SEM (Phillips XL30 Field Emission Scanning Electron Microscope) and four surface images taken at 500× magnification. Specimens were graded according to a previously published grading scale. If clarification was required specimens were also examined at higher magnification of 2000× and 5000×). Four pictures for each specimen (at 500× magnification) were used to calculate the percentage surface area covered by cilia using image analysis software and a previously validated technique. (Macintosh D, Cowin A, Adams D, Wormald P J, *Am. J. Rhinol.* 2005, 19(6), 557-81).

Cells from brushings were suspended in 1 ml of Dulbecco's culture medium and agitated to release cells into the culture medium. This was kept at 36.5° C. until CBF analysis was performed. Twenty μL from each specimen was placed on a microscope slide warmed to 36.5° C. and phase contrast microscopy was used. Ten cells per specimen were individually analyzed and the average of these taken as the CBF.

The well being of the sheep participating in this study was monitored by animal house veterinary staff experienced in handling sheep. Sheep were monitored four times a day for 2 days after the application of the agents for temperature, heart rate, mobility and oral intake. Following this they were monitored twice daily for the remainder of the study for mobility and oral intake.

Statistical Analysis

Two way ANOVA with Bonferroni correction post tests were conducted for analyzing epithelial height, re-epithelialization, re-ciliation, cilial grade and lateral nasal wall adhesion percentage and grade. Wilcoxon signed ranks test was used to analyze matched pairs in ethmoidal adhesion rates. Statistical significance was set at $p<0.05$.

The results are shown in FIGS. 1-5.

Results

The percentage of sheep in each group with adhesions on the lateral nasal wall over time is shown in FIG. 1. With the full thickness injury methods used the control group had an adhesion rate of 15%, the tissue factor group had an adhesion rate of 25%, while the SprayGel™ group had a rate of 10%. The hydrogel group had an adhesion rate of 10%, however this reduced to 5% at day 56 and remained at this level throughout the study. The hydrogel group had a significantly lower percentage of adhesions than the tissue factor group at day 56, 84 and 112 (5% vs 25%, $p<0.05$).

Figure 2:
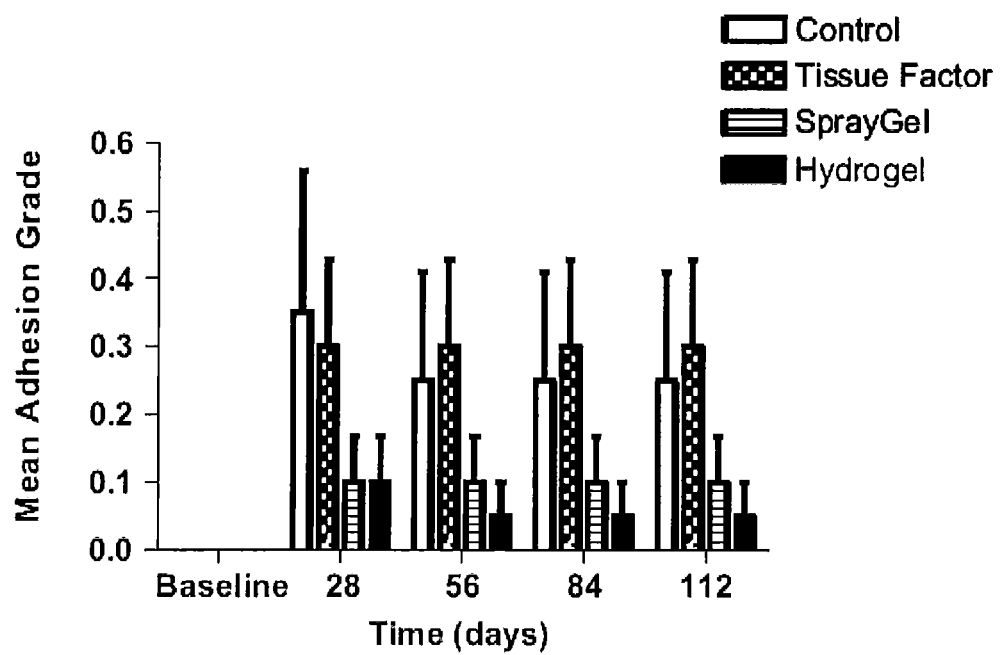
FIG. 2 is a graph showing the mean grade of adhesions on the lateral nasal wall (Example 6).

The mean grade of adhesions trended to less severe in the SprayGel™ group and even less severe in the hydrogel group, however these differences were not significant (FIG. 2).

Figure 3:
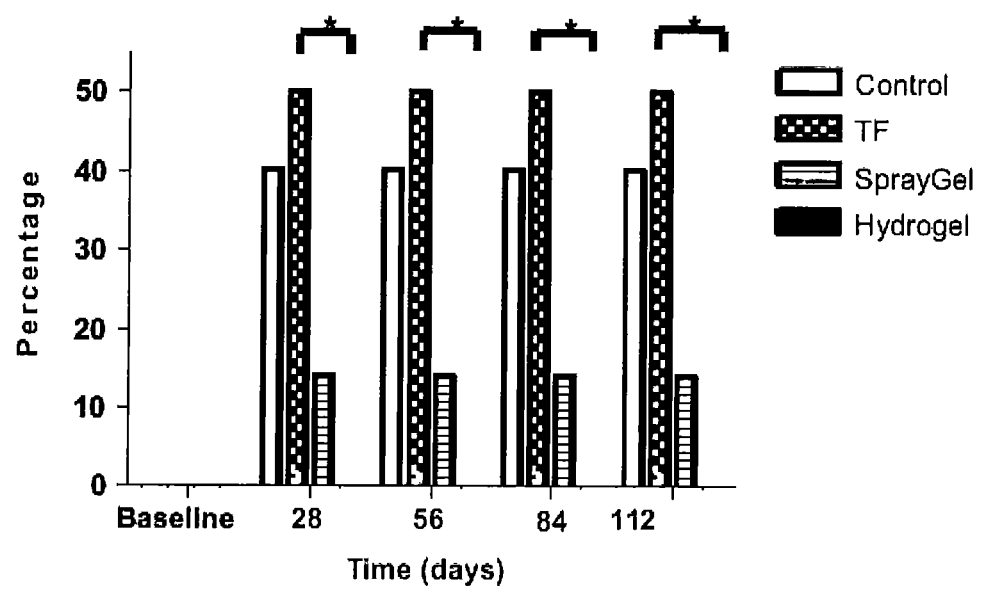
FIG. 3 is a graph showing the percentage of sheep in each group with ethmoidal adhesions (Example 6).
Figure 4:
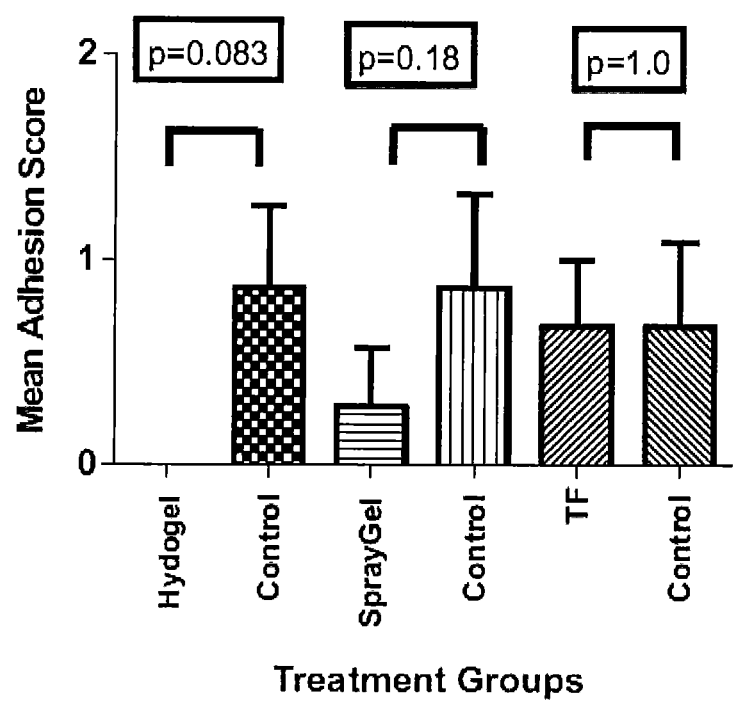
FIG. 4 is a graph showing the mean ethmoidal adhesion grade for all treatments compared to matched controls (Example 6).

Ethmoidal adhesion rates for each group over time are shown in FIG. 3. With the method described above a 40% ethmoidal adhesion formation rate was established in the control groups. This increased to 50% in the tissue factor group. The SprayGel™ group had a lower adhesion rate of 14%, however the hydrogel group experienced no ethmoidal adhesions. Despite the small numbers in this matched pairs study the hydrogel group experienced significantly less adhesions than the tissue factor group (0% vs 50%, $p<0.05$), see FIG. 4.

Figure 5:
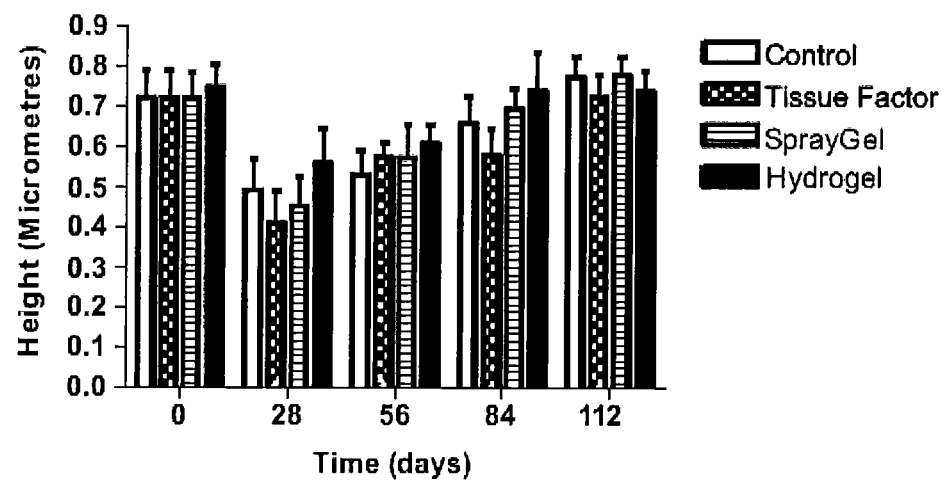
FIG. 5 is a graph showing a light microscopy comparison of epithelial height over time (Example 6).

When analyzing epithelial height over time with light microscopy, no significant difference was seen between the four groups (FIG. 5).

Figure 6:
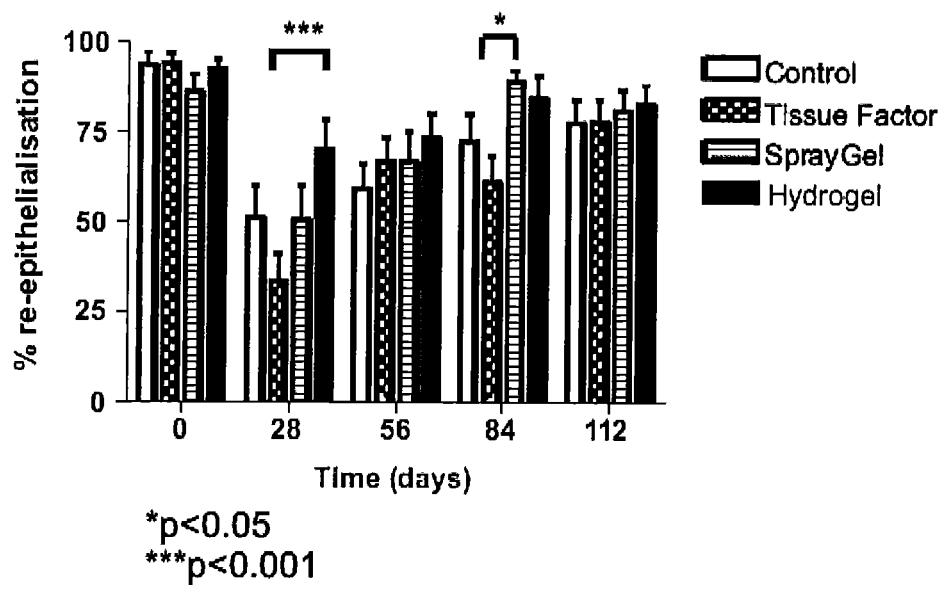
FIG. 6 is a graph showing a light microscopy comparison of the percentage re-epithelialisation (Example 6).

The percentage of mucosa which had re-epithelialized for each group can be seen in FIG. 6. The hydrogel group had a significantly greater percentage of re-epithelialization at day 28 compared to the tissue factor group (70% vs 33%, $p<0.001$). In addition, the SprayGel™ group had significantly greater re-epithelialization at day 84 than the tissue factor group (89% vs 61%, $p<0.05$).

Figure 7:
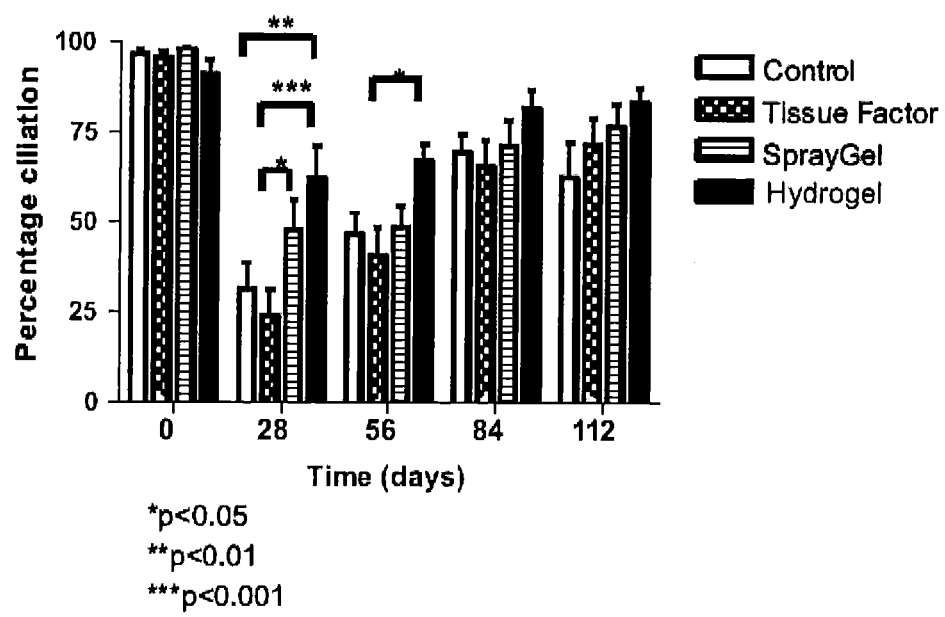
FIG. 7 is a graph showing a scanning electron microscopy comparison of the percentage surface area that was re-ciliated (Example 6).

FIG. 7 shows the percentage surface area (mean±standard deviation) that was re-ciliated over time for each of the four groups. At day 28 the hydrogel group was significantly more ciliated than control (62% vs 31%, $p<0.01$) and than tissue factor (62% vs 23%, $p<0.001$) while the SprayGel™ group also had significantly greater ciliated surface area than tissue factor (47% vs 23%, $p<0.05$). At day 56 the hydrogel group remained significantly more ciliated than the tissue factor group (67% vs 40%, $p<0.05$). Overall the hydrogel group trended towards improved re-ciliation, although this was not significant at all time points.

On average 1-2 specimens per group at each time point were unusable and given a grade of 5. Table 4 below shows the grading scale for scanning electron microscopy (SEM) images of sheep nasal cilia.

TABLE 4

| Grading scale for scanning electron microscopy (SEM) images of sheep nasal cilia | |
|---|---|
| Grade | Appearance on SEM |
| I | Normal cilia with normal orientation |
| II | Ciliated epithelium but disoriented |
| III | Stumps of cilia, regenerating cilia |
| IV | No identifiable cilia |
| V | Unusable (crust or clot covering epithelium) |

Figure 8:
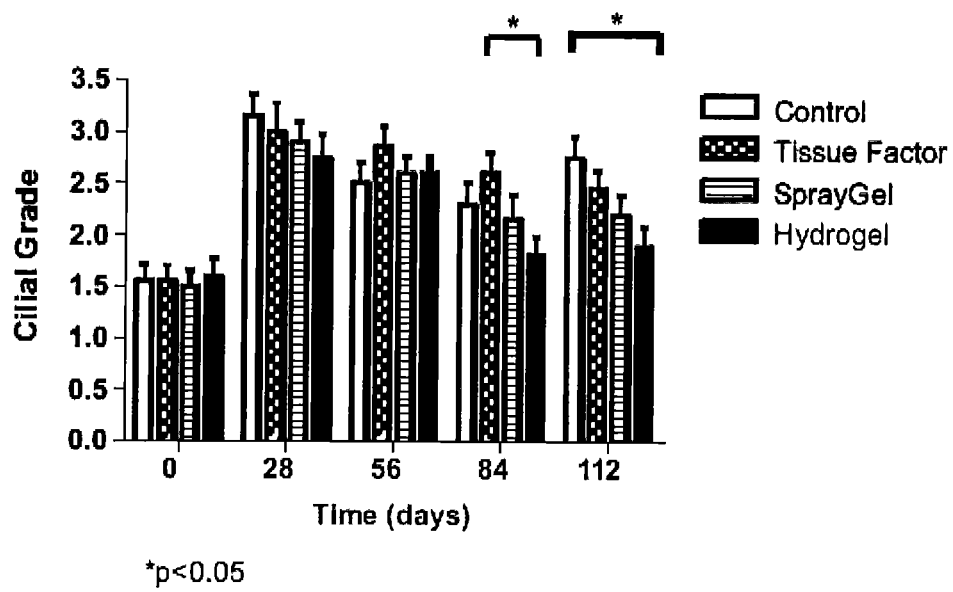
FIG. 8 is a graph showing a scanning electron microscopy comparison of cilial grade (Example 6).

Two-way ANOVA revealed no significant difference between the numbers of unusable specimens for each group at each time point therefore these were excluded from the subsequent analysis (data not shown). FIG. 8 shows the mean±SD cilial grade for each group at each time point. At day 84 the mean cilial grade for SprayGel™ was significantly better than for tissue factor (1.8 vs 2.6, $p<0.05$) and at day 112 the mean grade for hydrogel was significantly better than control (1.9 vs 2.7, $p<0.05$).

Figure 9:
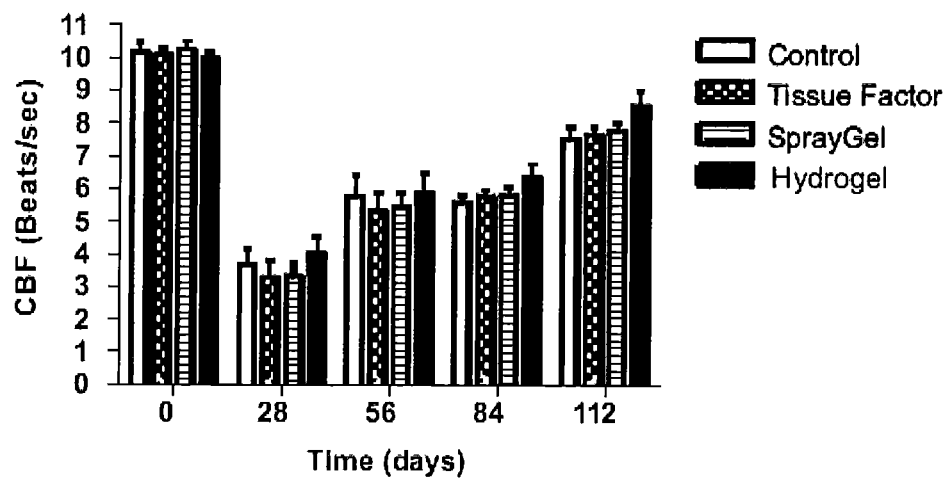
FIG. 9 is a graph showing the mean cilliary beat frequency (CBF) for each of the groups (Example 6).

Mean CBF was not significantly different between any of the four groups over time (FIG. 9). The hydrogel group trended towards improved ciliary function at all time points, however this was non-significant.

Importantly, none of the sheep experienced any adverse events during this study. There were no reports of fever, tachycardia, poor mobility or poor oral intake during the study period.

Discussion

Both SprayGel™ and the hydrogel of the invention exhibited some adhesion prevention properties. Hydrogel in particular showed significantly decreased adhesion formation both on the lateral nasal wall and the anterior ethmoids compared to tissue factor.

In terms of wound healing the results followed a similar pattern with both hydrogel and SprayGel™ having improved rates of re-epithelialization, re-ciliation and cilial grade compared to control and especially compared to tissue factor. The most striking feature of wound healing was the speedy recovery of the hydrogel groups epithelium, reflected in the significantly greater re-epithelialization and percentage surface area which was re-ciliated at day 28. Early on in this study the cilial grades of all four groups were not significantly different, however in the latter part of the study the hydrogel group had a significantly improved grade of cilia compared to tissue factor and control.

Example 7

Human Trials

A prospective randomised controlled pilot trial was performed. Six patients undergoing full house endoscopic sinus surgery were randomised to receive 20 ml of hydrogel while the contralateral side received no treatment. The solution was applied under endoscopic vision as a spray at the conclusion of the operating on each side. Bleeding after application was documented using standardised videoendoscopy and graded on 2 previously validated scales every 2 minutes up to a maximum of 10 minutes.

Results

Figure 10:
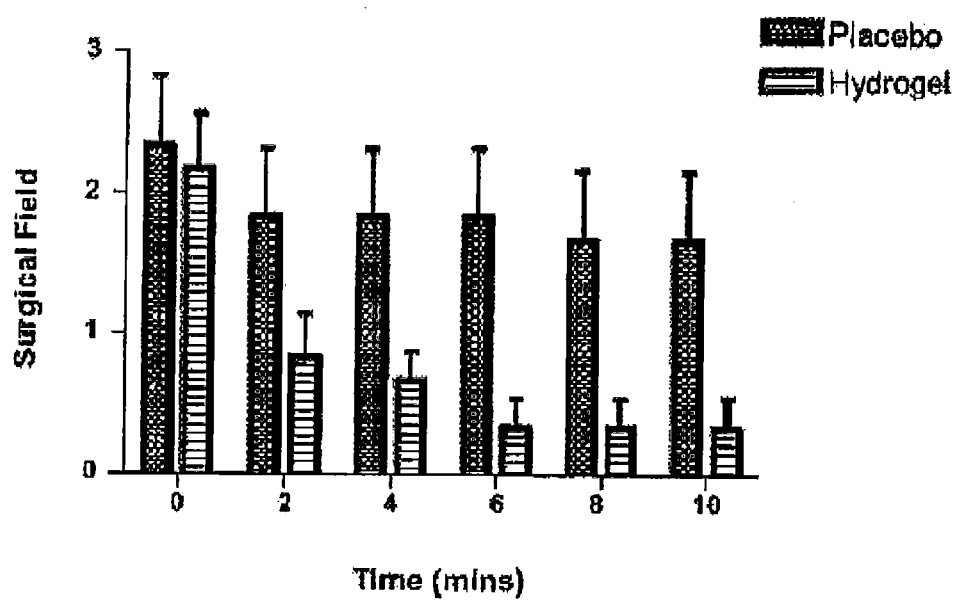
FIG. 10 is a graph showing the active vs placebo surgical field grade score using the Boezaart grading scale (Example 7).
Figure 11:
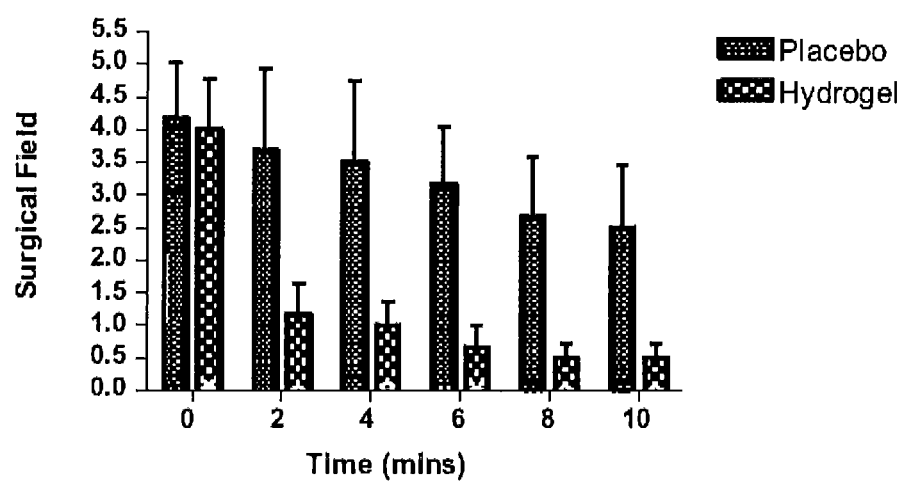
FIG. 11 is a graph showing the active vs placebo surgical field grading score using the Wormald grading scale (Example 7).

The hydrogel showed a clinically significant improvement in the surgical field at 4, 6, 8 and 10 minutes after application (see Table 5 and FIGS. 10 and 11).

TABLE 5

Bleeding scores of placebo vs active sides for 6 patients using surgical field bleeding scales

| Time | Boezaart bleeding scale | | | Wormald bleeding scale | | |
|---|---|---|---|---|---|---|
| (mins) | Placebo | Active | p value | Placebo | Active | p value |
| Baseline | 2.33 | 2.17 | 0.71 | 4.17 | 4 | 0.71 |
| 2 | 1.83 | 0.83 | 0.096 | 3.67 | 1.17 | 0.093 |
| 4 | 1.83 | 0.67 | *0.037 | 3.5 | 1 | 0.058 |
| 6 | 1.83 | 0.33 | *0.041 | 3.17 | 0.67 | 0.041 |
| 8 | 1.67 | 0.33 | *0.039 | 2.67 | 0.5 | 0.039 |
| 10 | 1.67 | 0.33 | *0.039 | 2.5 | 0.5 | 0.041 |

Further, the hydrogel of the invention was regarded by the surgeon as being more effective than placebo in 5 out of 6 cases, with one case regarded as no different. Other parameters known to affect haemostasis such as mean arterial pressure, heart rate and end tidal $CO_2$ were not significantly different between placebo and active sides.

Example 8

Effect of Hydrogel on Hemostasis Following Endoscopic Sinus Surgery in Sheep

Twenty one sheep (merino cross wethers) infested with the nasal bot fly *Oestrus ovus* participated in this study. Nasal bot fly infection was visually confirmed by nasal endoscopy and eosinophilic sinusitis documented with nasal swabs stained with Leishman stain. General anaesthesia was induced via injection of sodium thiopentone (19 mg/kg body weight) into the jugular vein. Endotracheal intubation then followed with anaesthesia maintained by inhalation of 1.5-2.0% halothane. The middle turbinate was removed prior to a standardized mucosal injury being created between the anterior ethmoid complex and the walls of the nasal cavity by the use of a microdebrider (Medtronic ENT, Jacksonville, Fla.). The duration of performance of the injuries on both sides were timed for a period of 30 seconds using a stopwatch. Immediately following mucosal injury a baseline surgical field grade was determined by an independent observer using the Boezaart Surgical Field Grading Scale (Boezaart A P, Van Der Meme J, Coetzee A, Comparison on sodium nitroprusside and esmolol induced controlled hypertension for functional endoscopic sinus surgery. (*Can J Anaesth* 1995, 42, page 373-376) (Table 6).

TABLE 6

Boezaart surgical field grading scale

| Grade | Assessment |
|---|---|
| 0 | No Bleeding (cadaveric conditions) |
| 1 | Slight Bleeding - no suctioning required |
| 2 | Slight Bleeding - occasional suctioning required. |
| 3 | Slight Bleeding - frequent suctioning required. Bleeding threatens surgical field a few seconds after suction is removed. |
| 4 | Moderate Bleeding - frequent suctioning required and bleeding threatens surgical field directly after suction is removed. |
| 5 | Severe Bleeding - constant suctioning required. Bleeding appears faster than can be removed by suction. Surgical field severely threatened and surgery usually not possible. |

Each nasal cavity was computer randomized to receive either no treatment (control) or 5 ml of the hydrogel of the invention applied to the ethmoid region immediately following baseline surgical field grade calculation. The hydrogel of the invention was stained with Fluorescein to aid in visualisation. A surgical field grade was calculated for each side every two minutes following baseline grading until bleeding ceased or up to a maximum of ten minutes observation.

Sheep were extubated and returned to their individual pens. Sheep were monitored three times daily, with variables such as food intact, nasal discharge and temperature observed. Trained animal handlers documented ongoing blood stained nasal discharge for the following 2 post-operative weeks. Each post-operative day all sheep were sedated and videoendoscopy performed documenting the presence of crusts/gel in wound site. This was then graded on a 3 point graduated scale from 0-2 (Table 7). Daily observation was continued for a period of 14 post-operative days.

TABLE 7

Ethmoid complex crust/gel dissolution

| Grade | Assessment |
| --- | --- |
| 0 | No crust/gel presence between ethmoid surfaces. |
| 1 | Less than 50% surface area of ethmoid complex covered by crust/gel. |
| 2 | More than 50% surface area of ethmoid complex covered by crust/gel. |

Results

The surgical field grade scores were analysed using GRAPHPAD PRISM™ and SPSS 11.0. As the data was not normally distributed, paired tests for non-parametric data using the Wilcoxon Signed Ranks Test were used to analyse the difference in surgical grade between sides. Bonferroni correction for multiple testing was applied to all analyses of surgical grade and statistical significance was set at $p<0.05$. Students T-test was used to compare means of time to complete hemostasis.

Comparison of Hemostasis with Control vs Hydrogel of the Invention Over Time

Figure 12:
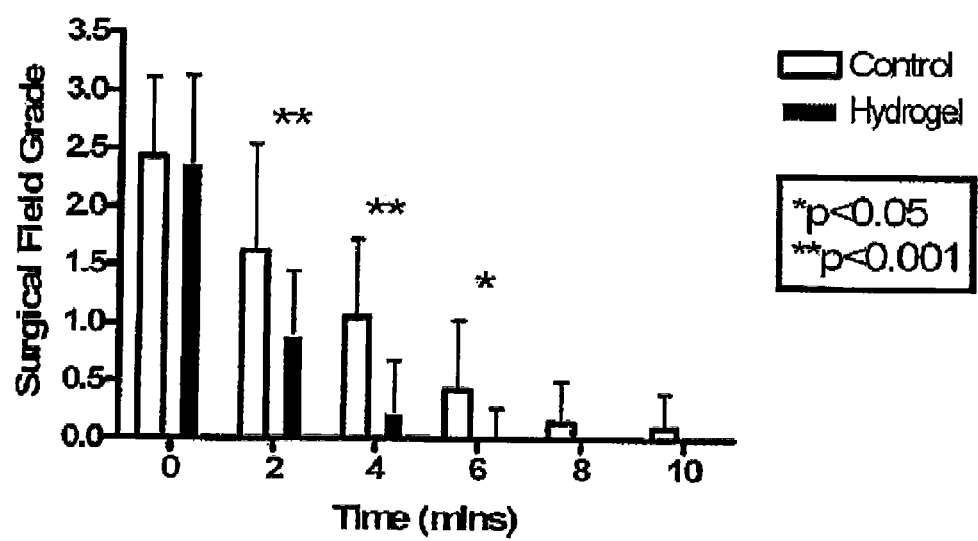
FIG. 12 is a graph showing the active vs control surgical field grading score using the Wormald grading scale (Example 8).

Twenty one sheep (merino cross wethers) participated in this part of the study. There was no significant difference in the baseline bleeding times between control vs hydrogel (2.4±0.67 vs 2.4±0.74). The hydrogel side was significantly more hemostatic at 2, 4 and 6 minutes after application. The Mean grading scores and 95% confidence intervals with control vs hydrogel were at 2 minutes—1.6(±0.92) vs 0.9(±0.53), at 4 minutes—1.0(±0.66) vs 0.24(±0.43) and at 6 minutes—0.4(±0.59) vs 0.048(±0.21) ($p<0.05$)(FIG. 12).

Time to Complete Hemostasis

Figure 13:
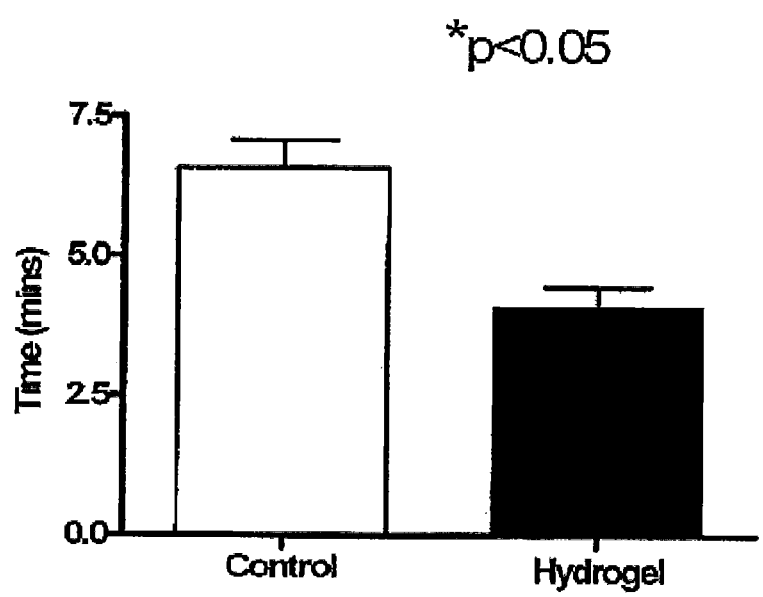
FIG. 13 is a graph showing the time to complete hemostasis for the active vs control (Example 8).

All the hydrogel sides had complete hemostasis by 6 minutes. Average time to hemostasis was significantly better for the hydrogel side at 4.09 (±1.61) vs 6.57 (±2.20) for the control sides (p=0.049) (FIG. 13). Ongoing bleeding on the control side was noted on 3 sides at 8 minutes and 1 at 10 minutes. This compares to no further bleeding past 6 minutes on the hydrogel side.

One sheep died on the 5$^{th}$ post-operative day. This was found to be from aspiration of stomach contents at post-mortem. There was no evidence of bleeding in this sheep. In the remaining sheep there was no ongoing blood stained nasal discharge past the first post-operative day, and no sheep was noted to have excessive ongoing bleeding requiring intervention.

Crust/Hydrogel Dissolution Scores

Figure 14:
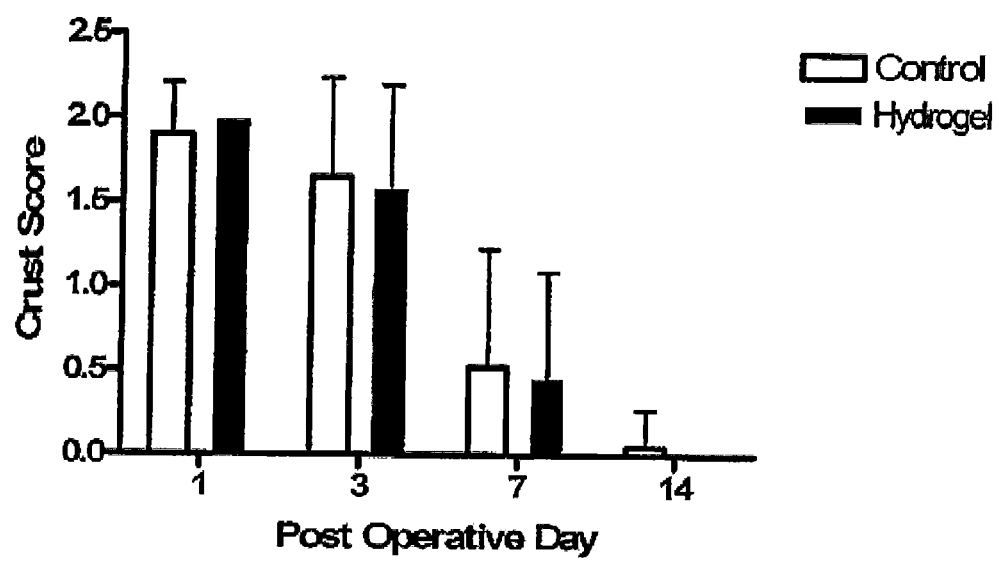
FIG. 14 is a graph comparing crust scores over time for active vs control (Example 8).

Twenty sheep participated in this part of the study. There was no significant difference between mean crust on the control side and the hydrogel dissolution scores on post operative day 1, 3, 7 and 14. The mean crust/hydrogel dissolution scores and 95% confidence intervals with control vs hydrogel were at day 1—2.0(±0.00) vs 1.9(±0.31), at day 3—1.6(±0.60) vs 1.65(±0.59), at day 7—0.47(±0.61) vs 0.53 (±0.70) and at day 14—0.00(±0.00) vs 0.05(±0.22) (FIG. 14).

Conclusion

In the sheep model of chronic sinusitis, the hydrogel of the invention significantly improves hemostasis compared to control at 2, 4 and 6 minutes following mucosal injury. It also displays similar crust dissolution characteristics when compared to control. Combining the known positive effects on wound healing, with its significant hemostatic effects, the hydrogel of the invention shows great potential as a post operative wound dressing following ESS in patients undergoing ESS.

INDUSTRIAL APPLICABILITY

The invention provides a water-based biodegradable hydrogel that can be applied to wounds to assist wound healing and prevention of adhesions. The hydrogels also have a positive effect on haemostasis and can be applied to bandages and field dressings to help stop bleeding in hemorrhaging trauma wounds, and post surgery.

The hydrogels of the invention are suitable for application during surgical procedures. Their use can improve the outcome of patients undergoing surgery.

The hydrogels of the invention can be easily prepared by non-medically trained people and can be used in emergency situations to prevent excessive blood loss in a victim until the victim can be transported to a medical facility.

The invention claimed is:

1. A composition comprising a dicarboxy-derivatized chitosan polymer cross-linked to an aldehyde-derivatized dextran polymer.

2. A composition according to claim 1 wherein the dicarboxy-derivatized chitosan polymer is cross-linked to the aldehyde-derivatized dextran polymer through an amine group of the dicarboxy-derivatized chitosan polymer and an aldehyde group of the aldehyde-derivatized dextran polymer.

3. A composition according to claim 1 wherein the composition forms a hydrogel within about 1 sec to about 5 minutes of mixing the dicarboxy-derivatized chitosan polymer and the aldehyde-derivatized dextran polymer in aqueous solution.

4. A composition according to claim 3 wherein the composition forms a hydrogel within about 1 sec to about 30 sec of mixing the dicarboxy-derivatized chitosan polymer and the aldehyde-derivatized dextran polymer in aqueous solution.

5. A composition according to claim 1 wherein the dicarboxy-derivatized chitosan polymer is N-succinyl chitosan.

6. A composition according to claim 1 further comprising an aqueous solution.

7. A composition according to claim 6 containing between about 2% to 10% w/v dicarboxy-derivatized chitosan polymer and between about 2% to 10% w/v aldehyde-derivatized dextran polymer.

8. A composition according to claim 1 in the form of a hydrogel.

9. A composition according to claim 8 containing between about 2% to about 8% w/v dicarboxy-derivatized chitosan polymer and about 2% to about 8% w/v aldehyde-derivatized dextran polymer.

10. A composition according to claim 8 containing about 5% w/v dicarboxy-derivatized chitosan polymer and about 5% w/v aldehyde-derivatized dextran polymer.

11. A composition according to claim 1 further comprising one or more biologically active agents.

12. A composition according to claim 11 wherein said one or more biologically active agents are selected from the group consisting of plasma proteins, hormones, enzymes, antibiotics, antiseptic agents, antineoplastic agents, antifungal agents, antiviral agents, anti-inflammatory agents, growth factors, steroids, cell suspensions, cytotoxins, and cell proliferation inhibitors.

13. A wound dressing comprising a composition according to claim 1.

14. A method of producing a composition of a dicarboxy-derivatized chitosan polymer cross-linked to an aldehyde-derivatized dextran polymer, comprising mixing an aqueous solution of a dicarboxy-derivatized chitosan polymer with an aqueous solution of an aldehyde-derivatized dextran polymer.

15. A method of preventing or reducing adhesion of tissue susceptible to adhesion formation comprising treating the tissue with a composition according to claim 1.

16. A method of accelerating or promoting wound healing comprising treating the wound with a composition according to claim 1.

17. A method of reducing or stopping bleeding of a wound comprising treating the wound with a composition of claim 1.

18. A method of treating a tissue comprising applying to said tissue:
   (a) an aqueous solution of a dicarboxy-derivatized chitosan polymer; and
   (b) an aqueous solution of an aldehyde-derivatized dextran polymer, such that (a) and (b) combine to form a cross-linked composition on said tissue.

19. A kit comprising:
   (a) dicarboxy-derivatized chitosan polymer, and
   (b) an aldehyde-derivatized dextran polymer.

* * * * *